(12) United States Patent
Wang et al.

(10) Patent No.: US 9,261,349 B2
(45) Date of Patent: Feb. 16, 2016

(54) OPTICAL IMAGING APPARATUS, OPTICAL IMAGING METHOD, APPARATUS FOR SETTING CHARACTERISTICS OF A LIGHT SOURCE, AND METHOD FOR SETTING CHARACTERISTICS OF A LIGHT SOURCE

(71) Applicant: KABUSHIKI KAISHA TOPCON, Tokyo (JP)

(72) Inventors: Zhenguo Wang, Fort Lee, NJ (US); Zhijia Yuan, River Edge, NJ (US); Kinpui Chan, Ridgewood, NJ (US)

(73) Assignee: KABUSHIKI KAISHA TOPCON, Tokyo (JP)

( * ) Notice: Subject to any disclaimer, the term of this patent is extended or adjusted under 35 U.S.C. 154(b) by 32 days.

(21) Appl. No.: 13/938,756

(22) Filed: Jul. 10, 2013

(65) Prior Publication Data
US 2014/0125988 A1 May 8, 2014

Related U.S. Application Data

(60) Provisional application No. 61/723,984, filed on Nov. 8, 2012.

(51) Int. Cl.
*G01B 9/02* (2006.01)
*A61B 3/10* (2006.01)
(Continued)

(52) U.S. Cl.
CPC ............ *G01B 9/02001* (2013.01); *A61B 3/102* (2013.01); *A61B 5/0066* (2013.01); *G01B 9/02091* (2013.01); *G01N 21/4795* (2013.01)

(58) Field of Classification Search
CPC .......... G01B 9/02091; G01B 9/02044; G01B 9/02004; G01B 2290/45; G01B 9/0209; G01B 9/02007; G01B 11/2441; G01B 21/4795; G01B 2021/1787; G01B 23/046; G01B 9/02083; A61B 5/7257; G01N 21/4795; G01N 2021/1787; G01N 23/046; G01J 3/51; G01J 3/45
USPC ......... 356/479, 497, 511, 477, 456, 450, 451, 356/495, 492, 489
See application file for complete search history.

(56) References Cited

U.S. PATENT DOCUMENTS 5,920,390 A * 7/1999 Farahi et al. .................. 356/477
6,104,946 A * 8/2000 Tsuchiya et al. .............. 600/476
(Continued)

FOREIGN PATENT DOCUMENTS

JP 2006-189424 A 8/2006

OTHER PUBLICATIONS http://omlc.org/news/jan98/skinoptics.html.*
(Continued)

*Primary Examiner* — Tarifur Chowdhury
*Assistant Examiner* — Mohamed K. Amara
(74) *Attorney, Agent, or Firm* — Pearne & Gordon LLP

(57) ABSTRACT

An embodiment provides a method for setting the characteristics of the light to be output from a light source unit for optical coherence tomography, using a computer. This method is performed by using relation information in which a representative wavelength, a wavelength range including said representative wavelength, and the light loss amount due to absorption by a medium are related to each other. This method includes the following steps: setting each value of a first parameter and a second parameter among the representative wavelength, the wavelength range, and the light loss amount; acquiring a value of a third parameter among the representative wavelength, the wavelength range, and the light loss amount other than said first parameter and said second parameter based on the set two values and said relation information; and outputting a value of said acquired third parameter.

2 Claims, 16 Drawing Sheets

(51) Int. Cl.
*A61B 5/00* (2006.01)
*G01N 21/47* (2006.01)

(56) References Cited

U.S. PATENT DOCUMENTS

| | | | |
|---|---|---|---|
| 7,450,242 | B2 | 11/2008 | Toida et al. |
| 8,825,140 | B2* | 9/2014 | Rice et al. ............... 600/473 |
| 2003/0088180 | A1* | 5/2003 | Van Veen et al. ......... 600/430 |
| 2003/0137669 | A1* | 7/2003 | Rollins et al. ............ 356/479 |
| 2006/0132791 | A1 | 6/2006 | Toida et al. |
| 2007/0195269 | A1* | 8/2007 | Wei et al. ................. 351/221 |
| 2007/0276269 | A1* | 11/2007 | Yun et al. ................ 600/504 |
| 2011/0176142 | A1 | 7/2011 | Hacker et al. |
| 2011/0199615 | A1* | 8/2011 | Sugita ...................... 356/456 |
| 2012/0113390 | A1* | 5/2012 | Torii et al. ................ 351/208 |
| 2014/0100440 | A1* | 4/2014 | Cheline et al. ............ 600/407 |

OTHER PUBLICATIONS

Marschall, Sebastian et al. "Investigation of the impact of water absorption on retinal OCT imaging in the 1060 nm range" IN: Biomedical Optics Express, Jul. 1, 2012, vol. 3, No. 7, p. 1620.

Extended European Search Report for EP Application No. 13004220.3, Jun. 12, 2014.
A. Ceyhun Akcay et al., "Spectral shaping to improve the point spread function in optical coherence tomography", Oct. 15, 2003 / vol. 28, No. 20 / Optics Letters pp. 1921-1923.
Jianmin Gong et al., "Optimal spectral reshaping for resolutionimprovement in optical coherence tomography", Jun. 26, 2006 / vol. 14, No. 13 / Optics Express pp. 5909-5915.
B. Povazay et al., "Enhanced visualization of choroidal vessels using ultrahigh resolution ophthalmic OCT at 1050 nm, Aug. 25, 2003 / vol. 11, No. 17 / Optics Express pp. 1980-1986".
Renu Tripathi et al., "Spectral shaping for non-Gaussian source spectra in optical coherence tomography", Mar. 15, 2002 / vol. 27, No. 6 / Optics Letters pp. 406-408.
Ying T. Pan et al., "Subcellular imaging of epithelium with time-lapse optical coherence tomography", Sep./Oct. 2007 vol. 12 5 Journal of Biomedical Optics pp. 050504-1-050504-3.
Zhijia Yuan et al., "On the possibility of time-lapse ultrahigh-resolution optical coherence tomography for bladder cancer grading", Sep./Oct. 2009 vol. 14 5 Journal of Biomedical Optics pp. 050502-1-050502-3.
Office action for JP 2013-146890 dated Jun. 23, 2015.

* cited by examiner

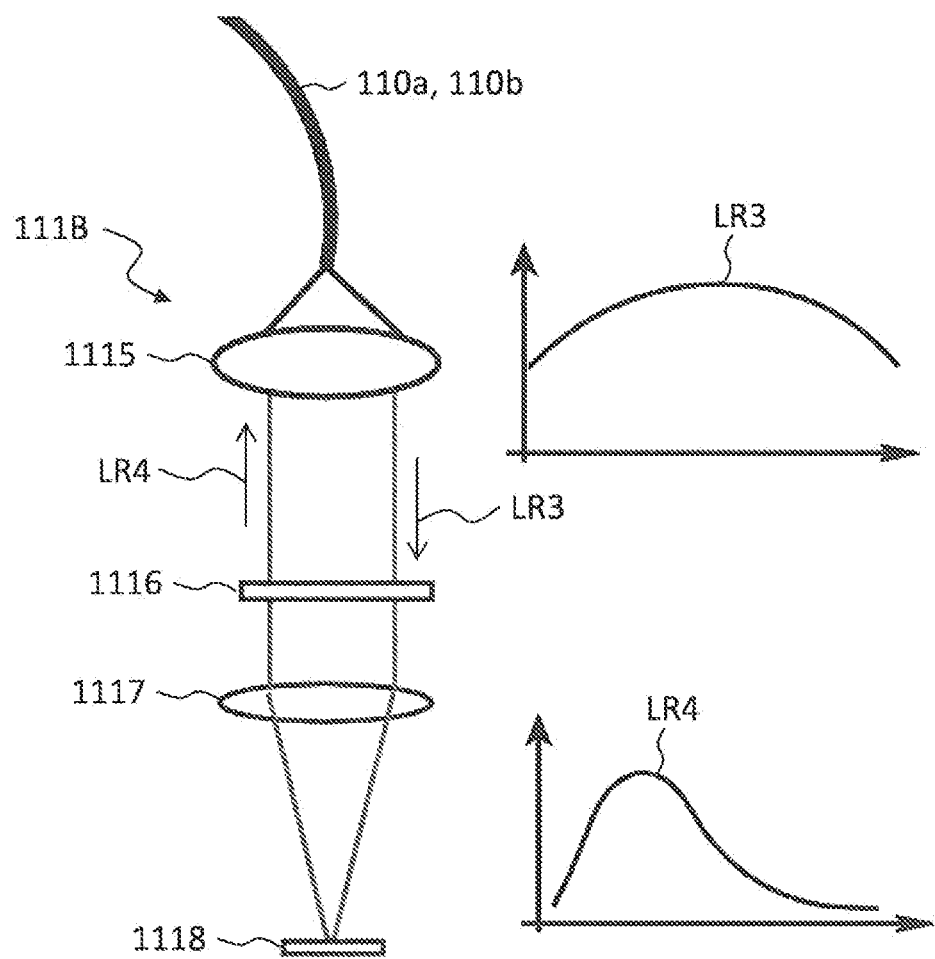

OPTICAL IMAGING APPARATUS, OPTICAL IMAGING METHOD, APPARATUS FOR SETTING CHARACTERISTICS OF A LIGHT SOURCE, AND METHOD FOR SETTING CHARACTERISTICS OF A LIGHT SOURCE

RELATED APPLICATION

This application is based upon and claims the benefit of priority from U.S. Provisional Patent Application No. 61/723,984, filed Nov. 8, 2012; the entire contents of which are incorporated herein by reference.

FIELD

The present invention relates to optical coherence tomography (OCT) technology.

BACKGROUND

OCT is an imaging technology for dividing the light output from a light source into signal light and reference light, detecting interference light obtained by superimposing the signal light having passed through an object with the reference light, and forming a tomographic image of the object based on the detection result. OCT includes a time domain method, spectral domain method, swept source method, etc. Time domain OCT is a tomographic imaging technology that acquires an A-line by sequentially scanning and detecting the pixels in the depth direction of the object. Spectral domain OCT is a tomographic imaging technology that acquires an A-line by sequentially resolving and detecting the spectrogram of the interference light. Swept source OCT is a tomographic imaging technology that acquires an A-line by using a light source whose output wavelength varies sequentially. In swept source OCT, the spectrogram of the interference light, which corresponds to the A-line, is acquired by detecting the interference light sequentially as the wavelength of the light source varies.

For OCT, the selection of wavelength and bandwidth of the light source is important. For example, the wavelength affects the penetration depth of the light into the object, while the bandwidth of the light source (wavelength range) affects the axial resolution (depth resolution). It should be noted that the value of the wavelength is represented by the value of a representative wavelength within the wavelength range to be used. In addition, the definitions of the representative wavelength and the wavelength range both depend on the measurement method used in the OCT system. For example, in an OCT system that employs the time domain system or spectral domain OCT method, a broadband light source such as a super luminescent diode (SLD) is used, wherein as a representative wavelength, a center wavelength of the light source is generally used, and as a wavelength range, a half width (full width at half maximum, FWHM) of the light source is generally used. On the other hand, in a swept source OCT system, a wavelength-sweeping light source is used. Therefore, as a wavelength range, such as a wavelength sweeping range of the light source, a range of spectrum of the light source to be detected by a detector, or a range of spectrum of an interference signal to be provided to the imaging processing, is used. In addition, as a representative wavelength of the swept source OCT system, a wavelength with a maximum intensity within the wavelength range is generally specified.

In addition, some media having light absorbing characteristics affect OCT measurement. For example, in the case of carrying out the OCT measurement of a human fundus, the measurement efficiency becomes low when the light is absorbed by a medium in the eye (particularly, water) and the spectrum is deformed by the absorption characteristics of the medium. According to the conventional OCT technology, this adverse effect is avoided by limiting the wavelength range of the light source used for the measurement to a wavelength region in which the absorption of light by the medium is small. For example, U.S. Pat. No. 7,450,242 discloses a technology, which, by taking into consideration the light loss due to water absorption and the two peaks of water absorption in the vicinity of a 1-µm wavelength (refer to FIG. 1), limits the useful wavelength range (wavelength sweeping range) to 0.98-1.20 µm. In addition, in the publication by B. Považay et al., "Enhanced visualization of choroidal vessels using ultra-high resolution ophthalmic OCT at 1050 nm, 25 Aug. 2003/Vol. 11, No. 17/OPTICS EXPRESS pp. 1980-1986", for similar reasons, a light source with a center wavelength of 1050 nm and a FWHM of 165 nm was used.

SUMMARY OF THE INVENTION

As described above, the conventional OCT technology limits the wavelength range in order to avoid light loss through a medium. Accordingly, the wavelength range cannot be arbitrarily increased in order to improve the axial resolution. On the other hand, since OCT serves to image fine structures of the object, the axial resolution is a very important factor.

In addition, when the wavelength range is simply increased, the spectral distribution is deformed due to the effect of light loss through a medium, and as a result, image quality may be significantly degraded. This degradation of the OCT image quality due to deformation of the spectral distribution is mainly represented as a side lobe artifact. According to the conventional OCT technology, it is not possible to get around with such degradation of image quality due to a deformation of the spectral distribution.

The object of the present invention is to provide an OCT technology capable of carrying out measurement with a high resolution even when there is light loss due to a medium.

An invention of an optical imaging apparatus configured to divide light output from a light source unit into signal light and reference light, detect interference light obtained by superimposing the signal light having passed through an object onto the reference light, and form a tomographic image of the object based on the detection result, wherein said light source unit is configured to output light with a wavelength range corresponding to coordinates positioned within a region whose border is a contour line indicating a predetermined light loss amount within the distribution information of the light loss amount due to absorption by a medium that is predefined in a space spanned by a first coordinate axis indicating a representative wavelength and a second coordinate axis indicating a wavelength range including said representative wavelength.

An invention according to the above, wherein said medium is substantially composed of water, and said coordinates are coordinates on a contour line indicating a region in which the excess loss amount over a reference loss amount is 4 dB, and passing through coordinates in the vicinity of a value 1124 nm on said first coordinate axis, or coordinates positioned in the negative direction of said first coordinate axis rather than said contour line.

Further to the above, an invention of an optical imaging apparatus wherein the component of said coordinates corresponding to said first coordinate axis is substantially 1050 nm.

In addition, an invention of an optical imaging method comprising the steps of: outputting light with a wavelength range corresponding to coordinates positioned within a region whose border is a contour line indicating a predetermined light loss amount within the distribution information of the light loss amount due to absorption by a medium that is predefined in a space spanned by a first coordinate axis indicating a representative wavelength and a second coordinate axis indicating a wavelength range including said representative wavelength; dividing the output light into signal light and reference light; generating interference light by superimposing the signal light having passed through an object onto the reference light; detecting the generated interference light; and forming a tomographic image of the object based on the detection result of the interference light.

An invention of an optical imaging apparatus configured to divide the light output from a light source unit into signal light and reference light, detect interference light obtained by superimposing the signal light having passed through an object onto the reference light, and form a tomographic image of the object based on the detection result, comprising a storage part configured to previously store relation information in which a representative wavelength, a wavelength range including this representative wavelength, and the light loss amount due to absorption by a medium are related to each other, wherein said light source unit outputs light including a wavelength range that is predetermined based on said relation information.

An invention of an optical imaging method, comprising the steps of: determining a representative wavelength and a wavelength range including said representative wavelength based on the relation information in which a representative wavelength, a wavelength range including this representative wavelength, and the light loss amount due to absorption by a medium are related to each other; outputting light including the determined wavelength range; dividing the output light into signal light and reference light; generating interference light by superimposing the signal light having passed through an object onto the reference light; detecting the generated interference light; and forming a tomographic image of the object based on the detection result of the interference light.

An invention of an optical imaging apparatus configured to divide the light output from a light source unit into signal light and reference light, detect interference light obtained by superimposing the signal light having passed through an object onto the reference light, and form a tomographic image of the object based on the detection result, comprising an optical member that converts the spectral distribution of the reference light such that the interference light based on the signal light having passed through a medium has a predetermined spectral distribution.

EFFECT OF THE INVENTION

According to the OCT technology of the present invention, it is possible to carry out measurement with a high resolution even when there is light loss due to a medium.

BRIEF DESCRIPTION OF THE DRAWINGS

FIG. 10B is a schematic diagram showing an example of a structure of an embodiment of an optical imaging apparatus.

DETAILED DESCRIPTION

Examples of embodiments of the present invention will be explained in detail with reference to the diagrams.

The present invention, in contrast with the conventional technology which aims to minimize the light loss due to absorption by a medium, takes into consideration how much light loss due to absorption by a medium is allowed depending on the configuration of the apparatus and the characteristics of the object. The present invention has been created based on such a new standpoint. Hereinafter, a principle to be obtained from this standpoint is described in addition to embodiment(s) based on this principle.

(Principle)

Hereinafter, the case in which water is used as a medium is described in detail, but the same argument applies to other media as well. Other media include a predetermined component of a liquid such as blood, various mixtures, an object to be measured (human eyes, etc.), etc.

Figure 1:
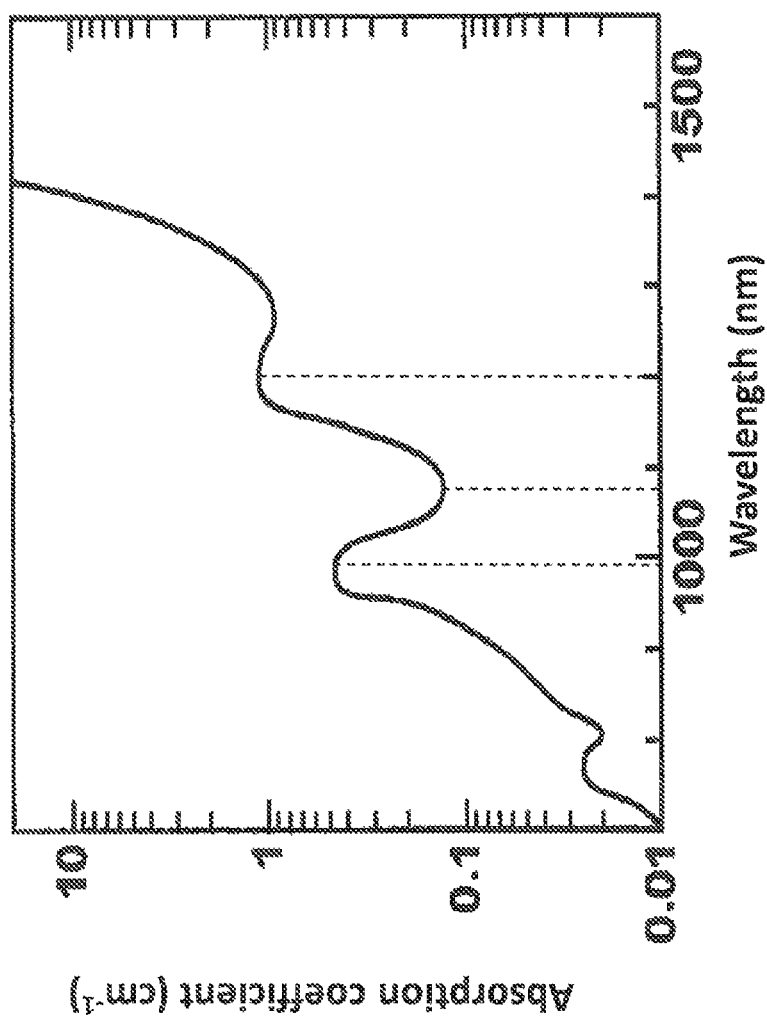
FIG. 1 is a graph showing the light absorbing characteristics of water.
Figure 2:
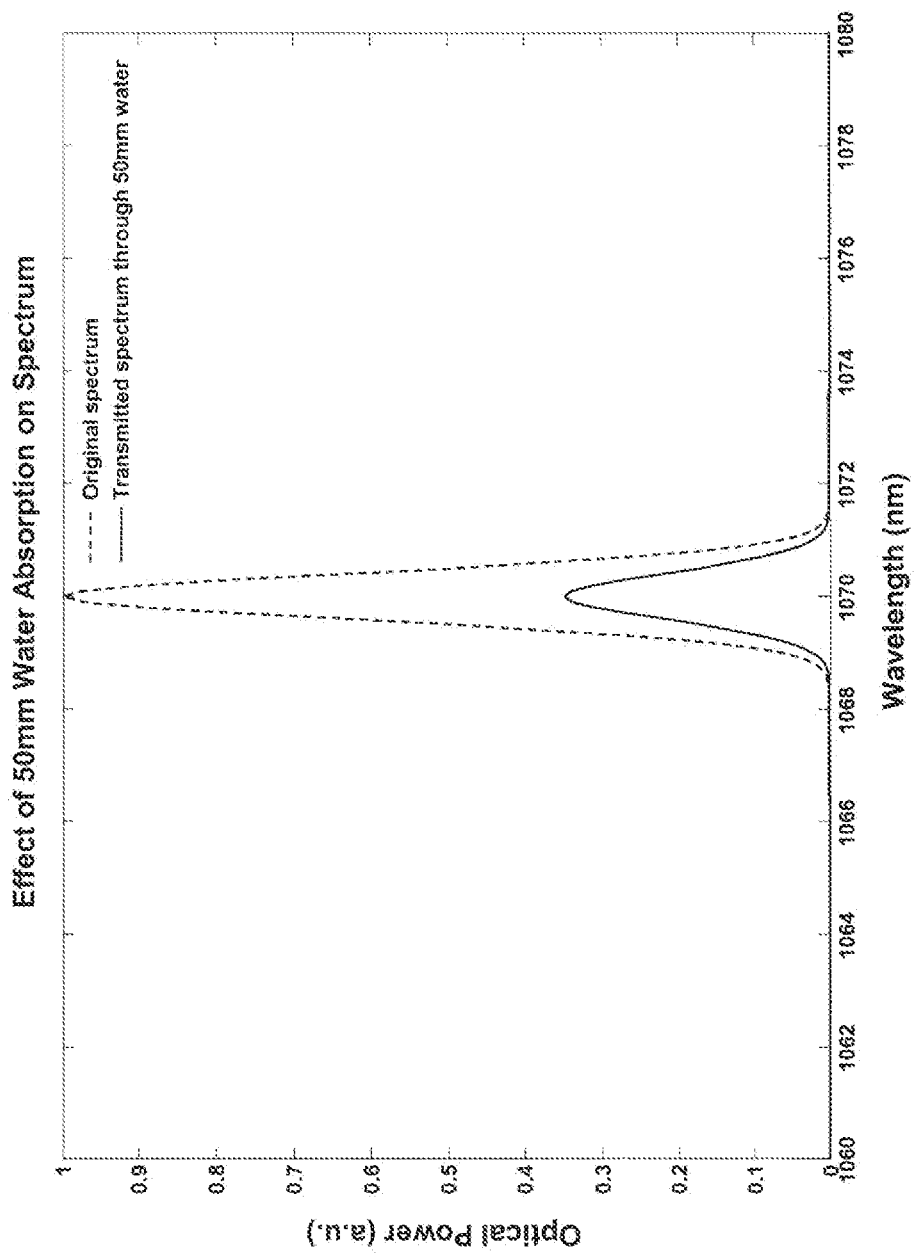
FIG. 2 is a graph showing the loss amount of light with prescribed wavelength due to water absorption.

As can be seen from the light absorption characteristics of water shown in FIG. 1, the light loss amount becomes minimal in the vicinity of a wavelength of 1070 nm. The calculated result of light loss amount at this wavelength is shown in FIG. 2. FIG. 2 depicts the amount of light loss when a light beam with a center wavelength of 1070 nm and a FWHM of about 2 nm (nearly monochromatic light) propagates through water of 50 mm thickness. The value of 50 mm is about twice the standard axial length of a human eye and corresponds to an intraocular distance in which signal light propagates in the case of measuring the fundus. The horizontal axis of FIG. 2 indicates the wavelength (nm), while the vertical axis indicates the light intensity (arbitrary unit a.u.). In addition, the graph shown with the broken line corresponds to the spectral distribution of the light beam incident into the water, while the graph shown with the solid line corresponds to the spectral distribution of the light beam passing through 50 mm of water.

As can be seen from a comparison between the two graphs shown in FIG. 2, the highest transmission under this condition is 0.35 (the peak value of the graph indicated by the solid line), which corresponds to −4.6 dB. Although a description is omitted, it is also confirmed that the transmission of light with other wavelength bands (the center wavelength and/or FWHM) does not exceed the abovementioned transmission. In this consideration, the quantum efficiency of a photo detector (for example, InGaAs detector is used) is also taken into account.

The abovementioned highest transmission corresponds to the light loss amount (reference loss amount) that is unavoidable in OCT measurement of human fundus using a wavelength range including a wavelength of 1070 nm. The inventors calculated the light loss amount (excess loss amount) to be added to the abovementioned reference loss amount with respect to various values of a representative wavelength (center wavelength) and a wavelength range (FWHM). The result is shown in FIG. 3.

Figure 3:
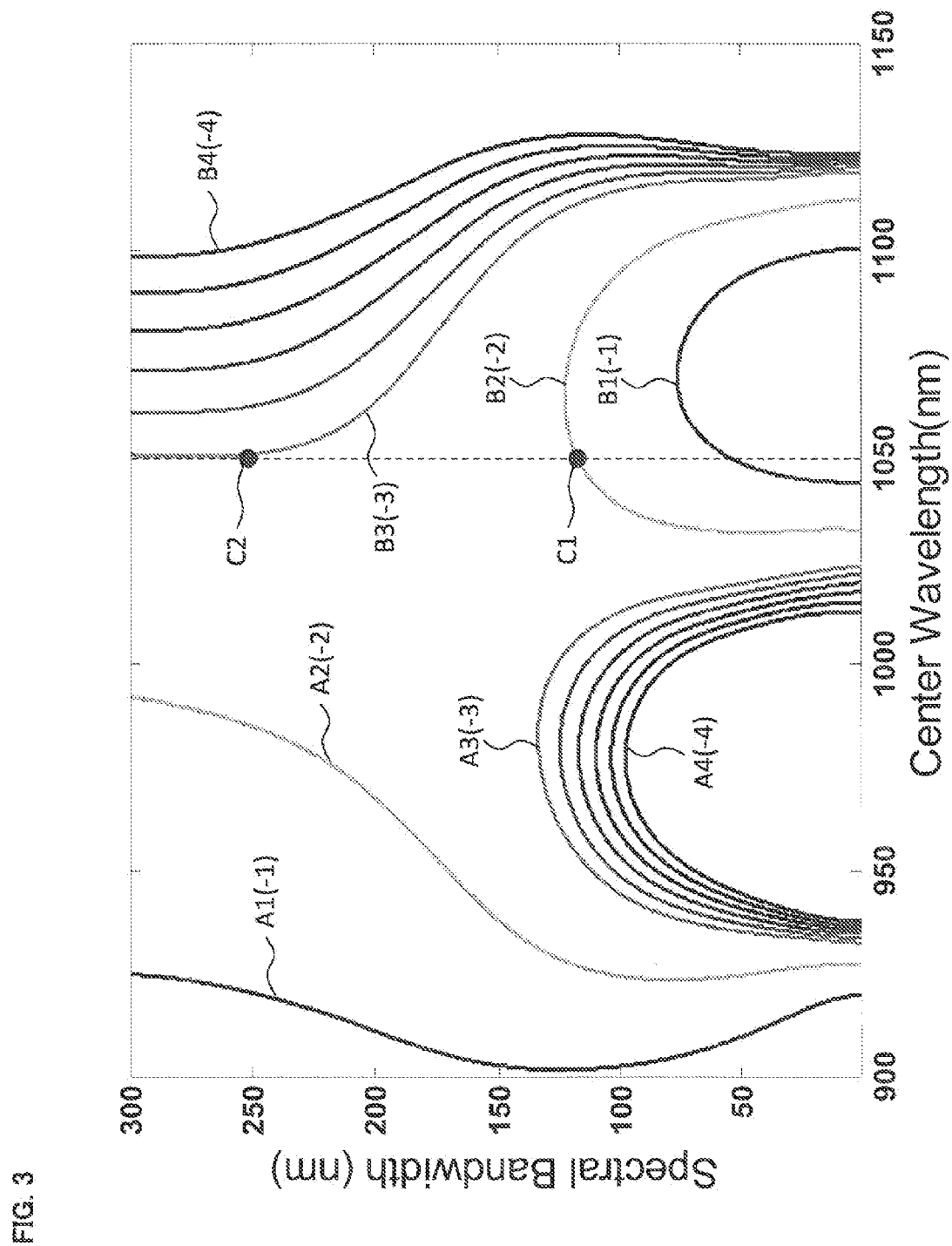
FIG. 3 is a graph showing distribution of excess loss amount due to water absorption.

FIG. 3 shows the distribution information that indicates the distribution of the excess loss amount with respect to a representative wavelength and a wavelength range. More specifically, the horizontal axis (first coordinate axis) shown in FIG. 3 corresponds to a representative wavelength (center wavelength (nm)), while the vertical axis (second coordinate axis) corresponds to a wavelength range (spectrum width, FWHM (nm)). The distribution of the excess loss amount is indicated by contour lines in a space spanned by the horizontal axis and the vertical axis. The contour lines A1 and B1 indicate the regions with an excess loss amount of 1 dB. The contour lines A2 and B2 indicate the regions with an excess loss amount of 2 dB. The contour lines A3 and B3 indicate the regions with an excess loss amount of 3 dB. The contour lines A4 and B4 indicate the regions with an excess loss amount of 4 dB. It should be noted that for those regions with an excess loss amount ranging from 3 dB to 4 dB, the contour lines are shown at a step of 0.2 dB.

FIG. 3 serves as an example to illustrate the distribution information, which is one example of the relation information. In the relation information, a representative wavelength, a wavelength range, and the light loss amount due to absorption by a medium are related to each other. The relation information is not necessarily continuous information such as the distribution information shown in FIG. 3, but also may be discrete information provided by a table.

As can be seen in FIG. 3, even if the values of the representative wavelength are the same, the excess loss amount changes depending on the wavelength range. In addition, even if the values of the wavelength range are the same, the excess loss amount changes depending on the value of the representative wavelength. Moreover, even if the values of the excess loss are the same, different regions (contour lines) exhibit distributions having different characteristics. Such knowledge is newly obtained as a result of taking a different viewpoint of the light loss into consideration from the conventional methods.

In the conventional technology, only the range of the wavelength (representative wavelength and wavelength range) with a small light loss amount is indicated. However, according to the relation information indicated by FIG. 3, by arbitrarily setting two parameters among the representative wavelength, the wavelength range, and the (excess) light loss amount, the third parameter can be acquired. In addition, by observing entire relation information, it is possible to grasp how these parameters should be set. For example, when a desired representative wavelength is chosen, it is possible to figure out the amount of light loss that will arise and a wavelength range that will yield a light loss of the desired amount. In addition, it is possible to figure out what a representative wavelength will be chosen in order to achieve a desired wavelength range (axial resolution). In addition, it is possible to figure out what a representative wavelength and a wavelength range will be adopted in order to achieve a desired light loss amount. These things are made possible only when referring to the abovementioned relation information. It can be said that, at least regarding this point, the present invention is completely different from the conventional technology.

Figure 4A:
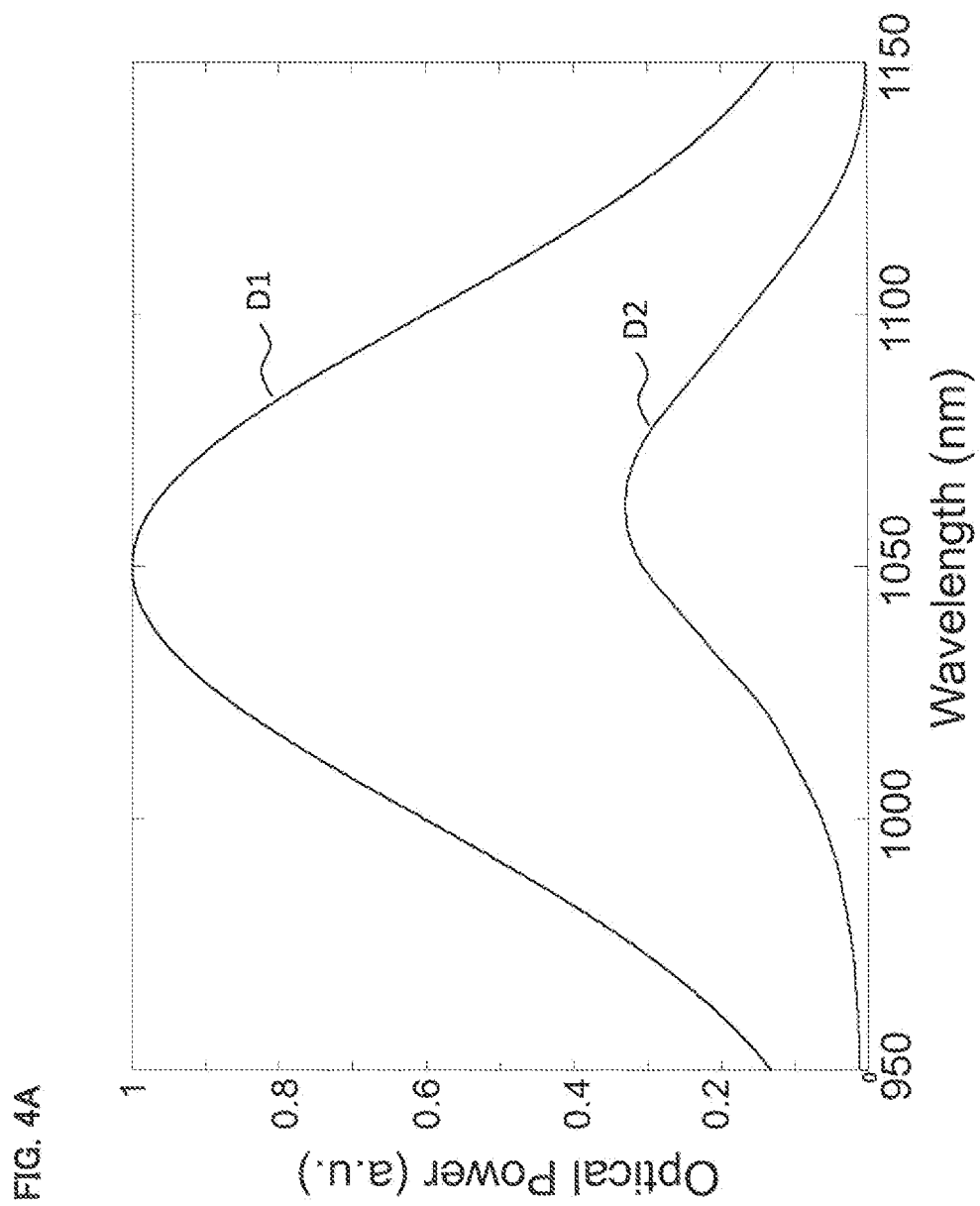
FIG. 4A is a graph showing a setting example of wavelength range based on distribution information.
Figure 4B:
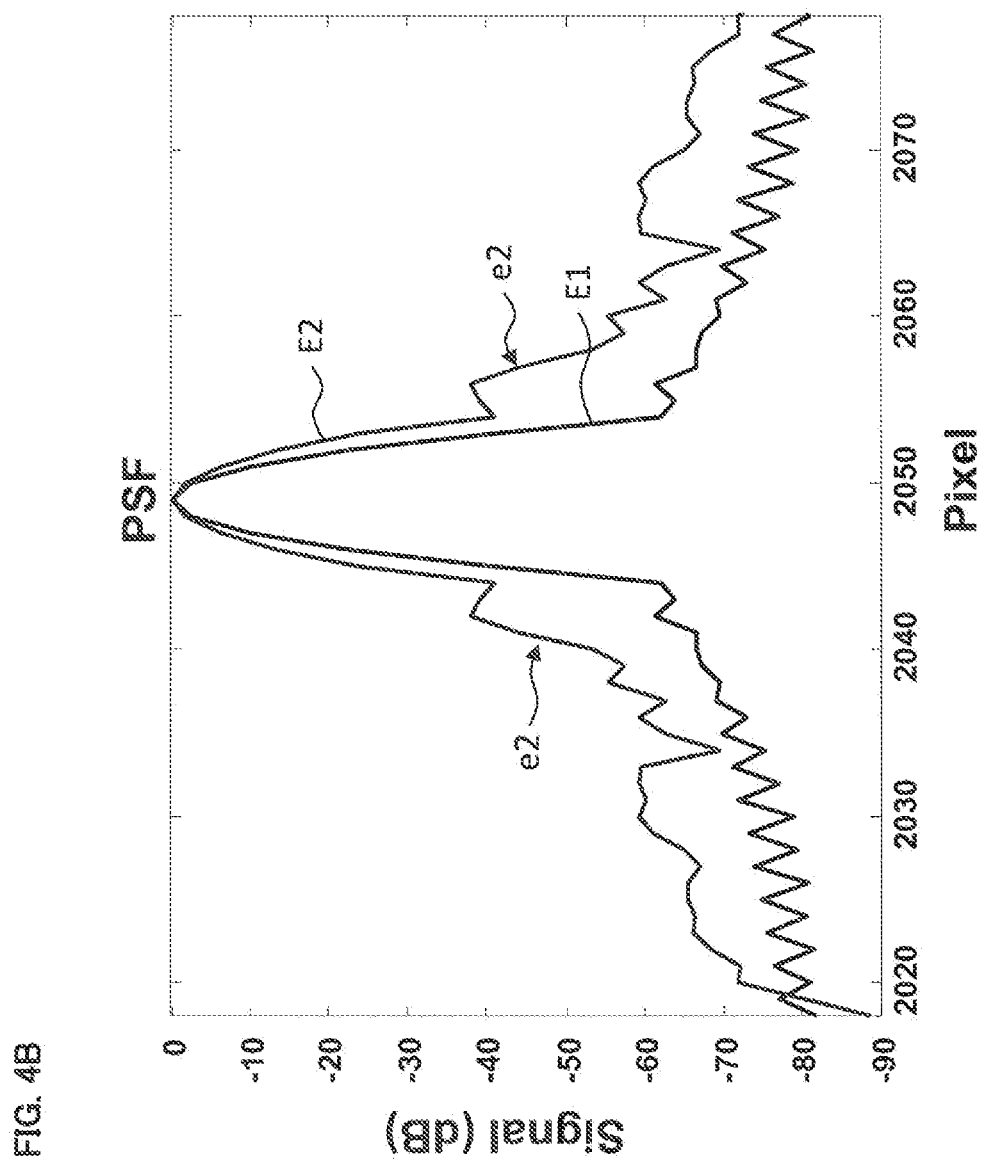
FIG. 4B is a graph showing a setting example of wavelength range based on distribution information.

An example of setting a wavelength band based on the distribution information indicated in FIG. 3 is described below. The first example is illustrated in FIG. 4A and FIG. 4B. The first example illustrates a case in which coordinates C1 (representative wavelength, wavelength range)=(1050, 117) of FIG. 3 are applied. The horizontal axis in FIG. 4A represents the wavelength (nm), while the vertical axis therein represents the light intensity (a.u.). In addition, the excess loss amount corresponding to the coordinates C1 is 2 dB. The symbol D1 indicates the spectral distribution of incident light into water, while the symbol D2 indicates the spectral distribution after this incident light travels through 50 mm of water. As can be seen from the graph of D2, the wavelength range (FWHM) of this light (transmission light) is 74.6 nm, and the axial resolution becomes 4.92 μm. Here, the axial resolution $l_c$ is calculated using the following formula based on a representative wavelength $\lambda_0$ and a wavelength range $\Delta\lambda$: $l_c=(2 \ln 2/\pi)\times(\lambda_0^2/\Delta\lambda)$.

FIG. 4B illustrates the point spread functions corresponding to the spectral distributions D1 and D2 indicated in FIG. 4A. The graph E1, which exhibits a narrower width, represents the point spread function corresponding to the incident light, while the graph E2 with a wider width represents the point spread function corresponding to the transmission light. The axial resolution based on the incident light is 4.02 μm, while the axial resolution based on the transmitted light is degraded to 4.92 μm. In the point spread function E2 of the transmitted light, side lobes e2 exceeding −40 dB are generated.

Figure 5A:
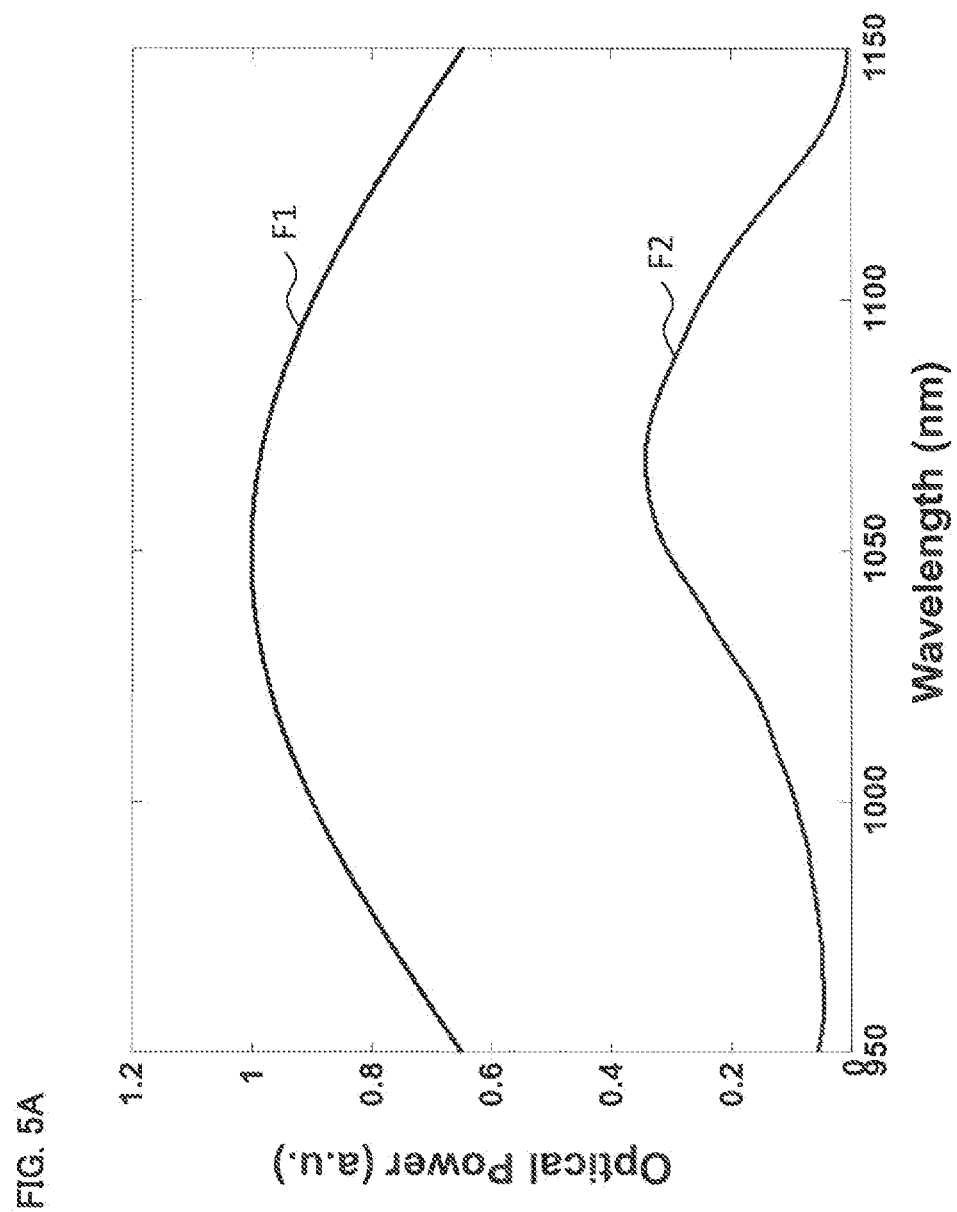
FIG. 5A is a graph showing a setting example of wavelength range based on distribution information.
Figure 5B:
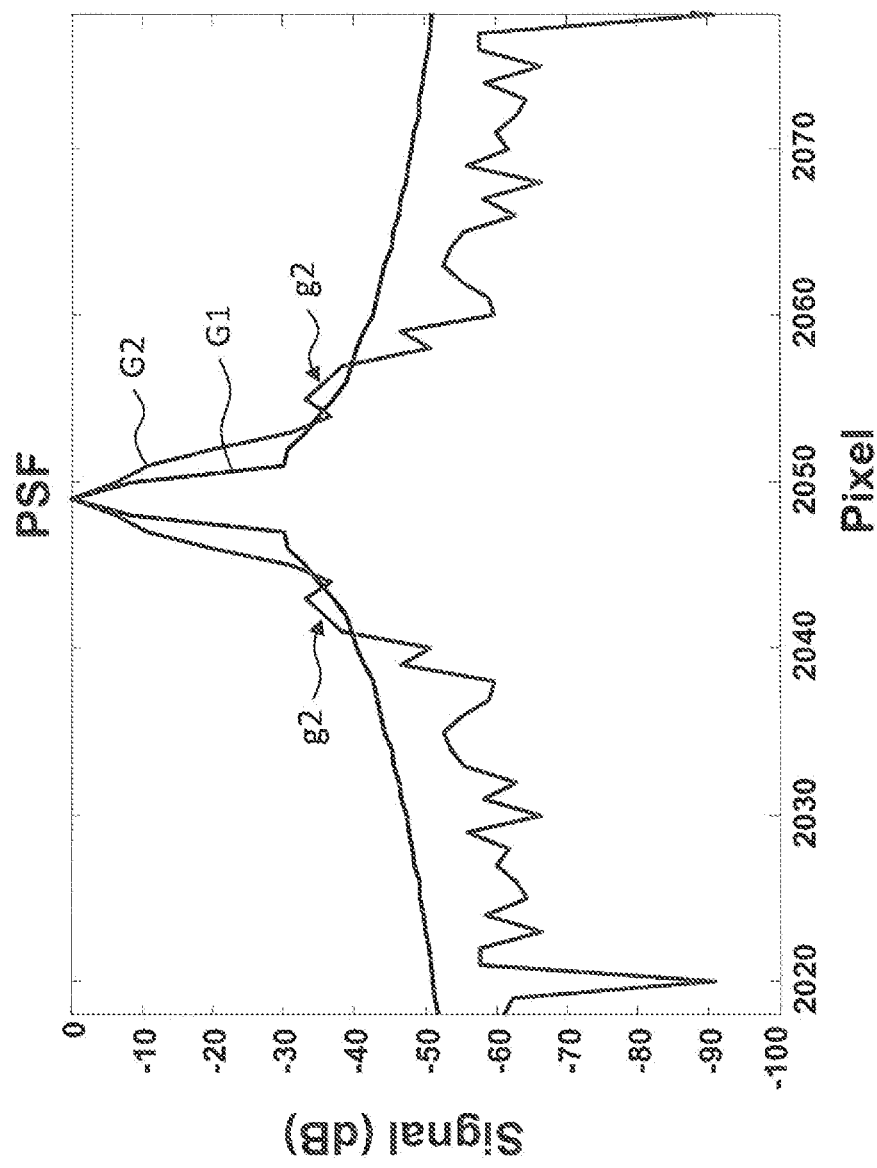
FIG. 5B is a graph showing a setting example of wavelength range based on distribution information.

The second example is illustrated in FIG. 5A and FIG. 5B. The first example illustrates a case in which the coordinates C2 (representative wavelength, wavelength range)=(1050, 253) used in FIG. 3 are applied. The excess loss amount corresponding to the coordinates C2 is 3 dB. The symbol F1 indicates the spectral distribution of incident light into water, while the symbol F2 indicates the spectral distribution after this incident light travels through 50 mm of water. As can be seen from the graph F2, the wavelength range (FWHM) of the transmitted light is 90.7 nm, while the axial resolution is 2.39 μm.

FIG. 5B illustrates the point spread functions corresponding to the spectral distributions of the spectral distributions F1 and F2 illustrated in FIG. 5A. The graph G1, which exhibits a narrower width, represents the point spread function corresponding to the incident light, while the graph G2 with a wider width represents the point spread function corresponding to the transmitted light. The axial resolution based on the incident light is 2.01 μm, while the axial resolution based on the transmitted light is 2.39 μm. In the point spread function G2 of the transmitted light, side lobes g2 of nearly −30 dB are generated.

As described above, a user is capable of arbitrarily selecting a representative wavelength, a wavelength range, and a light loss amount by using the distribution information (relation information) indicated in FIG. 3 as constrained conditions. Particularly, it is also possible to select a wavelength range in excess of the limitation set by the conventional technology from the view point of light absorption loss due to a medium. This is because the present invention now makes it possible to grasp the relation between the wavelength range and other parameters (particularly, light loss amount). In addition, in the abovementioned example, a wavelength band near 1000 nm is described; however, the same principle can be applied to other wavelength bands, for example, an 800 nm band and a 1300 nm band, as well.

Taking detection efficiency and the side lobe into consideration, it can be seen that light absorption loss by a medium may yield adverse effects on the improvement of OCT image resolution. It is preferable for the achievement of high image quality that the data corresponding to an A-line (A-profile) will have a dynamic range of about 45 dB. This requires a suppressing of the side lobes to a level as demanded by the dynamic range.

However, the quantification of absorption characteristics across the entire spectrum of incident light has not been carried out before. According to a simulation carried out by the inventors, it is confirmed that, in the best transmission window near a wavelength of 1070 nm, without sacrificing detection efficiency exceeding 2 dB, a spectrum width can be widened to about 123 nm. Accordingly, a value of about 5.2 µm is obtained as the highest axial resolution value (in air). In order to further improve axial resolution by widening the wavelength range, it is feared that further absorption due to water may cause adverse effects on detection sensitivity.

The inventors found that a 1-µm wavelength OCT with an ultrahigh resolution (axial resolution 2-3 µm) can be realized while keeping the additional loss of sensitivity below a predetermined value (for example, 3 dB) in the imaging of human eyes. This finding is also true in the case that includes a wavelength of shorter than 980 nm.

The processing method for compensating the distortion of spectral distribution due to water absorption is described. As can be seen from the above description, in order to achieve both desirable detection efficiency and axial resolution, it is important to use a light source having an optimal spectral distribution and wavelength range. In addition, distortion of the spectral distribution due to water absorption causes adverse effects on the performance of an OCT system. Particularly, the axial resolution is degraded and an artifact such as a side lobe of a point spread function, etc. is generated. Accordingly, it is preferable to improve the performance of an OCT system as well as the OCT image quality by applying a method capable of compensating for the effects of water absorption.

As a method of compensating for the effects of water absorption, a methodology named spectral shaping is known. Spectral shaping includes the technique that carries out shaping digitally (numerically) by software-based method, the technique that shapes a light source spectrum by hardware-based method, and the technique that acquires interference light having a desired spectral shape by adjusting the spectral distribution of the reference light (a technique referred to as cross spectral shaping).

Spectral shaping method using software is a method of obtaining a digital shaping filter for shaping the measured spectrum (cross spectrum) into an ideal shape such as a Gaussian shape, Hamming window, etc. For example, this method is described in the following documents.

Renu Tripathi et al., "Spectral shaping for non-Gaussian source spectra in optical coherence tomography", Mar. 15, 2002/Vol. 27, No. 6/OPTICS LETTERS pp. 406-408

Jianmin Gong et al., "Optimal spectral reshaping for resolution improvement in optical coherence tomography", 26 Jun. 2006/Vol. 14, No. 13/OPTICS EXPRESS pp. 5909-5915

According to spectral shaping method using hardware, a device for shaping the spectrum of light output from a light source (shaping filter) is provided. This device can be, for example, a programmable spectrum processor. For example, this method is described in the following document.

A. Ceyhun Akcay et al., "Spectral shaping to improve the point spread function in optical coherence tomography", Oct. 15, 2003/Vol. 28, No. 20/OPTICS LETTERS pp. 1921-1923

According to cross spectral shaping method, a filter for deforming the spectral distribution of the reference light is used. For example, this method is described in the following documents. It should be noted that in the embodiment to be described later, the spectral distribution of the reference light is also deformed; however, the present technology is different from the conventional technology in that the effect of absorption by a medium is taken into consideration. That consideration of the effect of absorption is available only by using the relation information as indicated in FIG. 3. Accordingly, the embodiment is substantially different from those based on the conventional cross spectral shaping method.

Ying T. Pan et al., "Subcellular imaging of epithelium with time-lapse optical coherence tomography", September/October 2007 Vol. 12 5 Journal of Biomedical Optics pp. 050504-1-050504-3

Zhijia Yuan et al., "On the possibility of time-lapse ultrahigh-resolution optical coherence tomography for bladder cancer grading", September/October 2009 Vol. 14 5 Journal of Biomedical Optics pp. 050502-1-050502-3

As described above, the conventional technology does not take into consideration the characteristics of the object as a key factor for optimizing the spectral shaping method.

According to the conventional spectral shaping method using software, changes in the spectral distribution of signal light cannot be corrected as a function of depth (in other words, changes cannot be corrected for each depth position). Further, since the method is carried out after data acquisition, read out noise may be increased through the photoelectric conversion and digitalization processes.

The conventional spectral shaping method using hardware requires a deformation of the spectral distribution of the light source, making it potentially impractical to implement.

The objective of conventional cross spectral shaping method is to correct the chromatic aberration. Meanwhile, the standard for optimization is to maximize the full width at half maximum of the cross spectrum that is detected by an optical spectrum analyzer. Furthermore, it is necessary to perform the optimization by separately adjusting the spectral distribution of the reference light and the spectral distribution of the signal light. In addition, the conventional cross spectral shaping method takes into consideration only the characteristics of the optical system of an apparatus, while not taking into consideration the characteristics of the measurement object that may significantly influence the measurement.

Summary of Embodiment(s)

According to this embodiment, the issues in the conventional technology are solved by the matters described below.

This embodiment serves to optimize cross spectral shaping by taking into consideration the characteristics of an object (light absorption characteristics of a medium).

According to this embodiment, cross spectral shaping is optimized by providing a physical filter in a reference arm of the interference optical system. In contrast to conventional cases in which a digital (numerical) filter is used, the physical filter changes the cross spectrum prior to photoelectric conversion. Therefore, the occurrence of errors and noise during photoelectric conversion can be avoided.

The optimization process of this embodiment is carried out based on the qualitative analysis of the light transmission rate of an object containing water and the detection of a desired cross spectrum (for example, spectrum having a Gaussian shape).

In this embodiment, in addition to the abovementioned filter processing that is performed prior to photoelectric conversion, a digital (numeric) shaping of the cross spectrum after data acquisition may be carried out as well. This additional spectral shaping is carried out in the same way as the abovementioned conventional technology.

Figure 6:
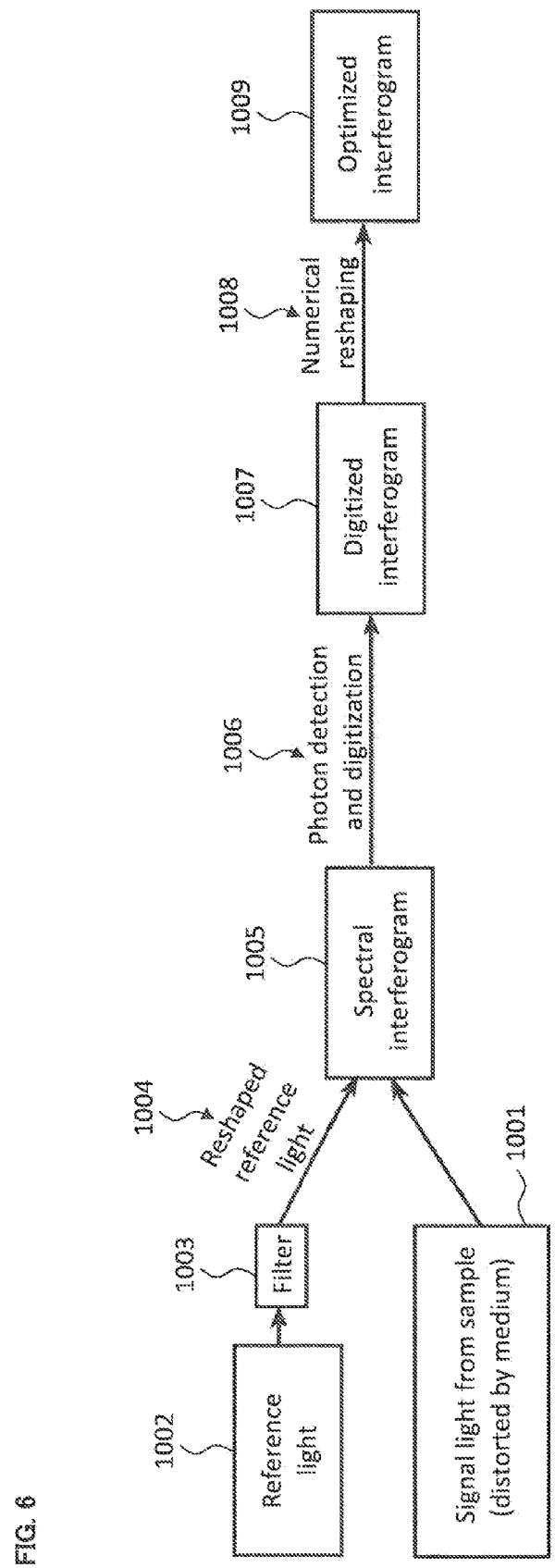
FIG. 6 is a schematic diagram for explaining a method according to an embodiment.

The content of processing according to the embodiment is described. An example of the processing content is illustrated in FIG. 6. The spectral distribution of signal light 1001 having passed through an object (sample) is distorted by the effects of absorption due to a medium within the object (for example, water in the eye). On the other hand, the spectral distribution of reference light 1002 is shaped by passing through a filter 1003. The spectrum-shaped reference light 1004 is superimposed with the signal light 1001 to generate interference light. The spectrum interferogram 1005 of this interference light is detected by a photodetector to be converted to analog electric signals, and further, the analog electric signals are digitized (1006). Image data is formed based on the interferogram 1007 obtained in this way. It should be noted that, as illustrated in FIG. 6, by additionally carrying out a numerical (digital) spectral shaping 1008, namely, a spectral shaping by software, image data may be formed based on the optimized interferogram 1009 obtained by this spectral shaping.

In order to realize such processing, the transmission characteristics (transmission function) $T_r(\lambda)$ of the filter 1003 for preferably performing spectral shaping of the reference light 1002 are necessarily obtained. In this embodiment, the transmission function $T_r(\lambda)$ is obtained by using the following formula.

$$T_r(\lambda) = S_c(\lambda)^2 / [S_s(\lambda)^2 \cdot A_w(\lambda)]$$

Here, $S_c(\lambda)$ indicates the spectral distribution of the desired cross spectrum, $S_s(\lambda)$ indicates the spectral distribution of output light from a light source, and $A_w(\lambda)$ indicates the transmission characteristics (transmission ratio) of an object (a medium), respectively. It should be noted that, $A_w(\lambda)$, based on the graph $\alpha(\lambda)$ of light loss due to water absorption illustrated in FIG. 1 and the distance L in which signal light travels through a medium (for example, 50 mm), is defined as $\exp(-\alpha(\lambda) \cdot L)$. In addition, $S_s(\lambda)$ is arbitrarily set based on a Gaussian shape and Hamming window, for example.

In this embodiment, corrections are only made by spectral shaping of the reference light. By applying the optimum spectral distribution of the reference light to adjust the reference light, a preferable axial resolution can be achieved, while an ideal cross spectrum (for example, Gaussian shape spectrum) capable of effectively suppressing the side lobe of a point spread function can be obtained as well.

The method for changing the spectral distribution of a reference light may include any methods illustrated by the examples given below. First, as a filter to be installed inside the reference arm, a focusing lens and a reference mirror, for which the relative distance can be changed, are provided. The focusing lens has a chromatic aberration, such that, by changing the distance between these elements, the spectral distribution of the light reflected by the reference mirror can be changed.

An optical filter that is customized so as to have transmission characteristics obtained by the abovementioned method can be installed inside the reference arm. Due to this optical filter, the spectral distribution of the reference light can be changed.

By arranging an optical element with polarization-dependent transmission characteristics inside the reference arm and adjusting the polarization state of the reference light, the spectral distribution of the reference light can be changed. As an alternate means, a preferable spectral distribution can be obtained by means of combining the spectrum characteristics of a light source and a polarization beam splitter.

Hereinafter, the advantages of abovementioned processing are described by providing the following examples.

Figure 7A:
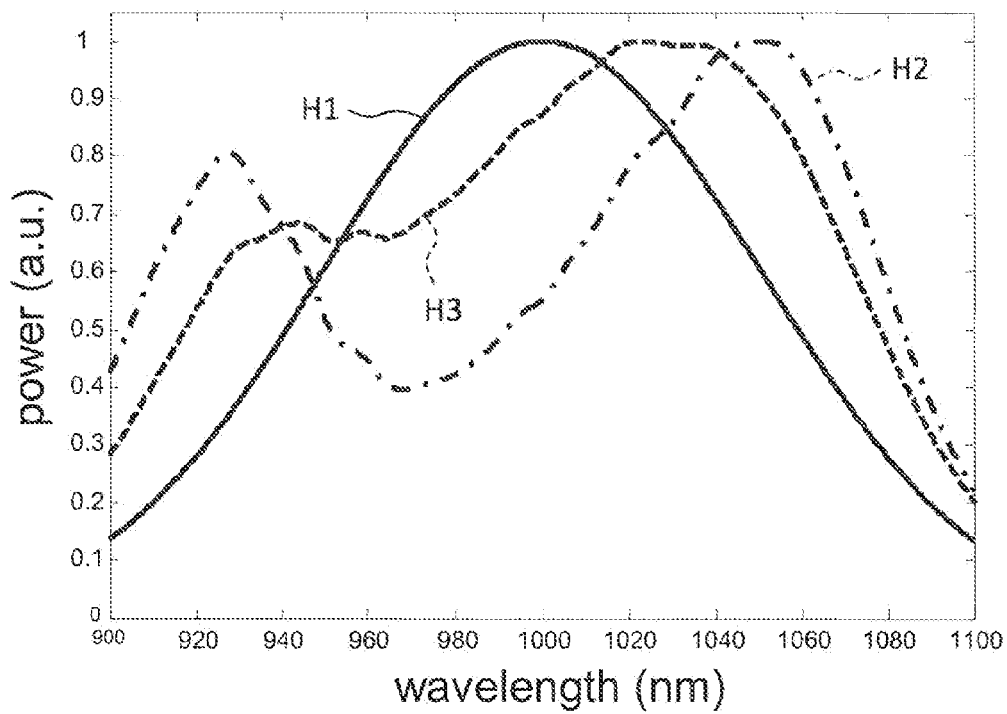
FIG. 7A is a graph for explaining an effect of a method according to an embodiment.
Figure 7B:
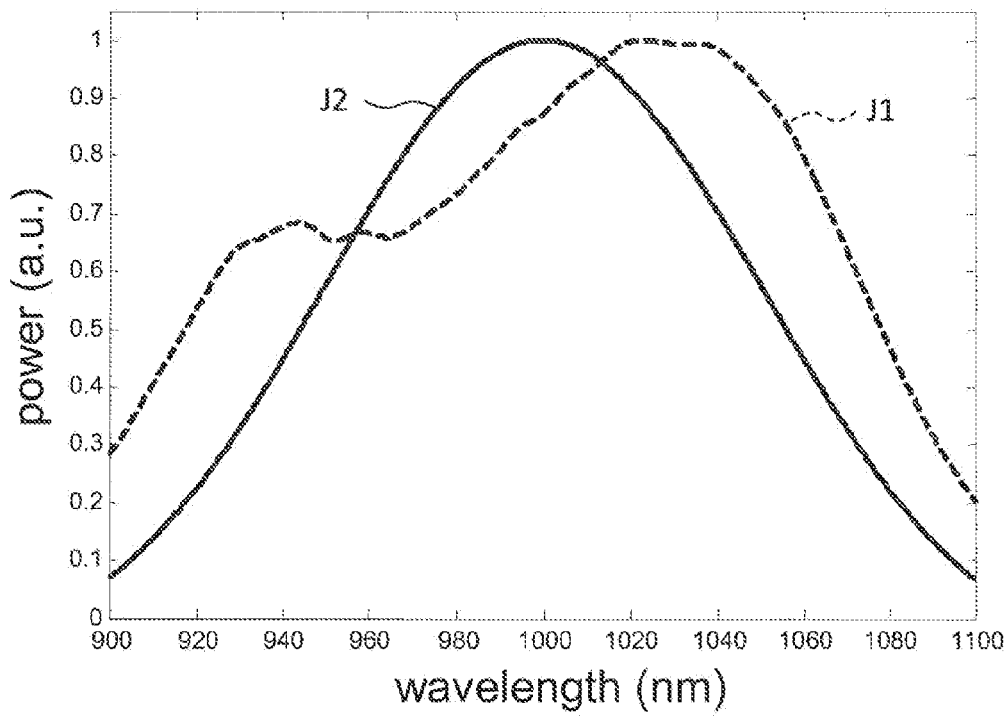
FIG. 7B is a graph for explaining an effect of a method according to an embodiment.
Figure 7C:
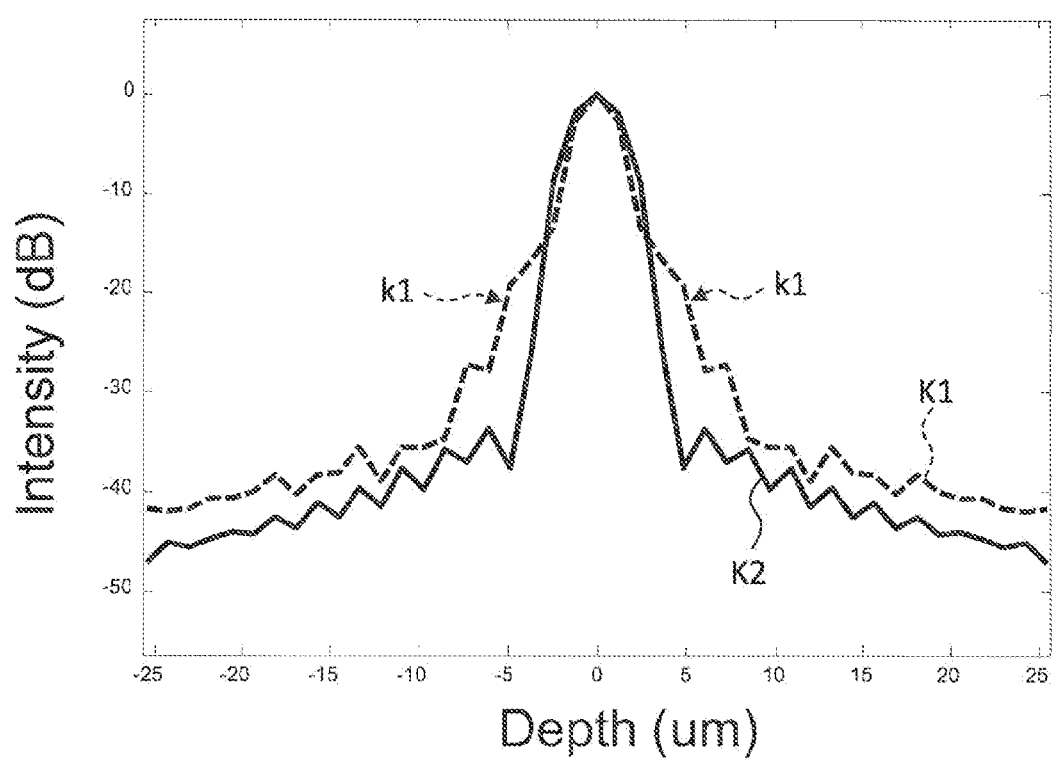
FIG. 7C is a graph for explaining an effect of a method according to an embodiment.

With reference to FIGS. 7A, 7B, and 7C, the first example is described. In the present example, a representative wavelength of 1050 nm and a wavelength range (FWHM) of 100 nm are applied. In FIG. 7A, three graphs H1, H2, and H3 are illustrated. The solid-line graph H1 indicates the spectral distribution of a light source with a Gaussian shape spectrum. The dashed-dotted line graph H2 indicates the spectral distribution of the reflected light (signal light) from the object affected by water absorption. The broken line graph H3 indicates a cross spectrum that is distorted by water absorption.

FIG. 7B illustrates two graphs J1 and J2. The broken-line graph J1 indicates a cross spectrum distorted by water absorption. The solid-line graph J2 indicates a cross spectrum corrected by the method according to the embodiment. As is obvious from FIG. 7B, according to the method of the embodiment, the cross spectrum J1 with distortion is corrected into cross spectrum J2 that shows a substantially Gaussian shape.

The point spread functions corresponding to the two cross spectrums J1 and J2 are illustrated in FIG. 7C. Point spread functions K1 and K2 correspond to the cross spectrum J1 whose distortion is not corrected and to the cross spectrum J2 whose distortion is corrected, respectively. In the corrected point spread function K2, the side lobes k1 generated in the uncorrected point spread function K1 are suppressed. According to the correction indicated in the present example, the axial resolution is slightly degraded from 3.7 μm to 4.3 μm; however, the side lobes are suppressed by an amount of about 18 dB.

Figure 8A:
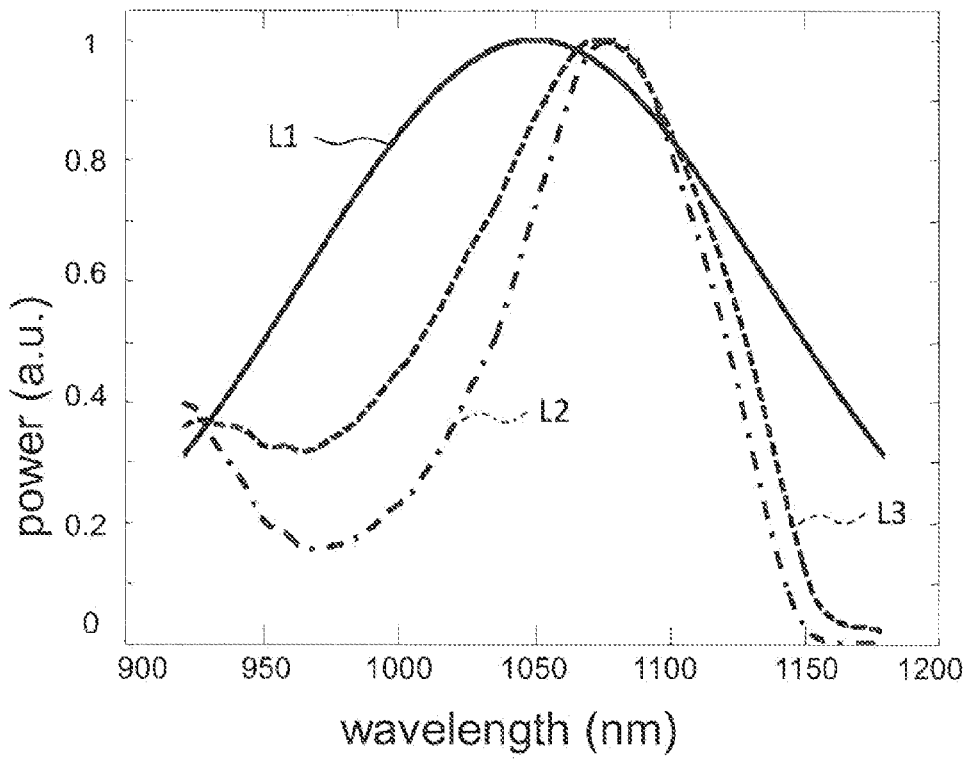
FIG. 8A is a graph for explaining an effect of a method according to an embodiment.
Figure 8B:
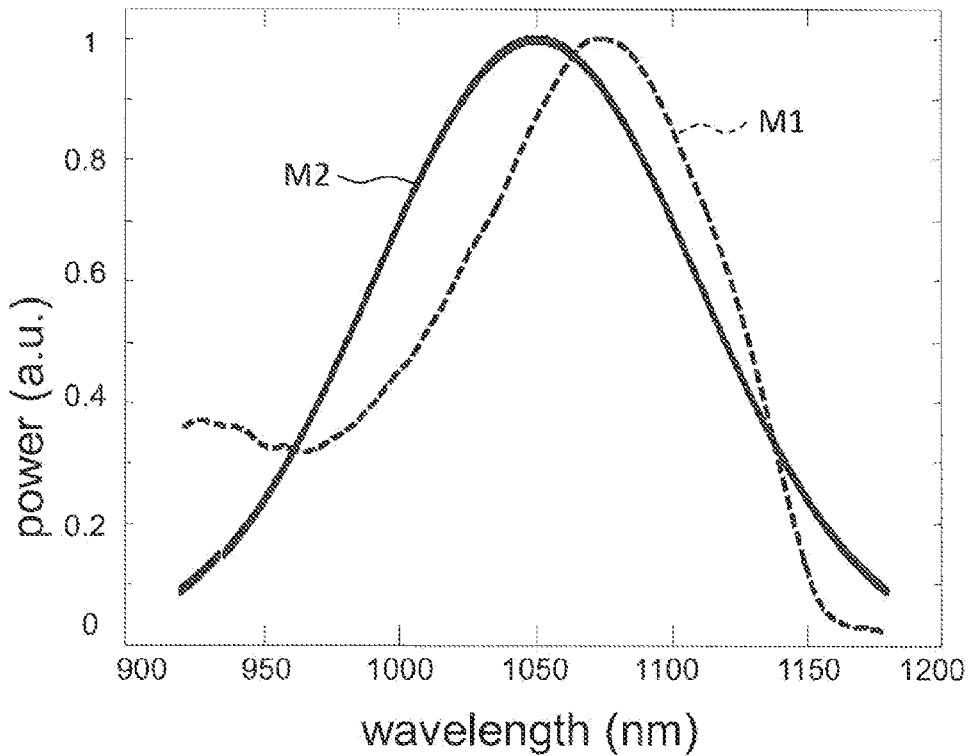
FIG. 8B is a graph for explaining an effect of a method according to an embodiment.
Figure 8C:
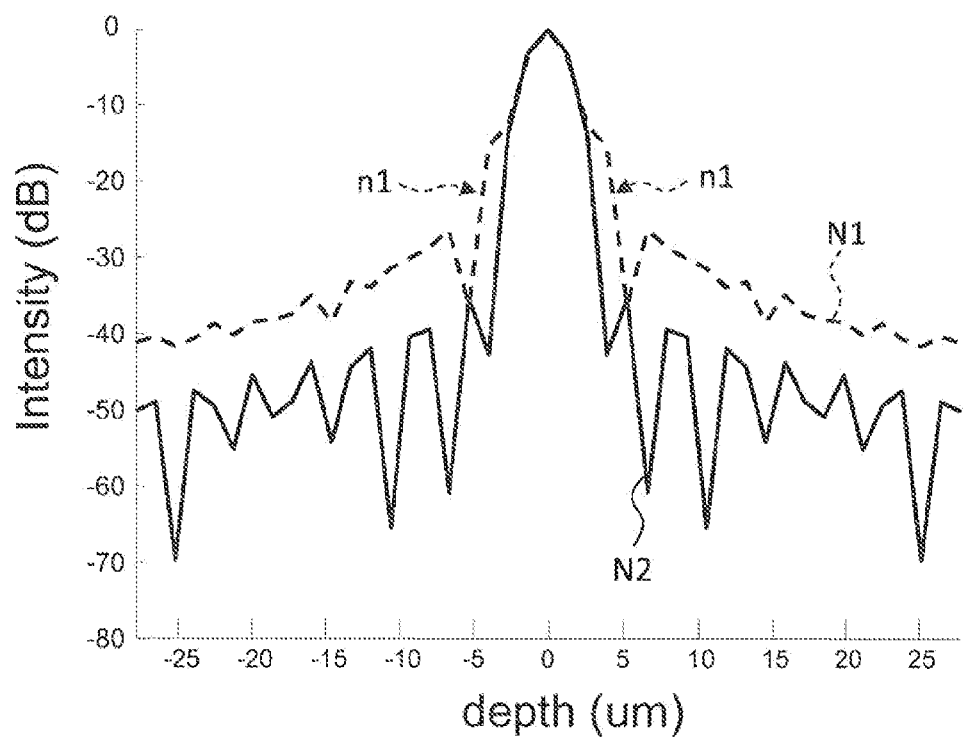
FIG. 8C is a graph for explaining an effect of a method according to an embodiment.

With reference to FIGS. 8A, 8B, and 8C, the second example is described. In the present example, a representative wavelength of 1050 nm and a wavelength range (FWHM) of 200 nm are applied. In FIG. 8A, three graphs L1, L2, and L3 are illustrated. The solid-line graph L1 indicates the spectral distribution of a light source with a Gaussian shape spectrum. The dashed-dotted line graph L2 indicates the spectral distribution of reflected light (signal light) from the object affected by water absorption. The broken line graph L3 indicates a cross spectrum that is distorted by water absorption.

FIG. 8B illustrates two graphs M1 and M2. The broken-line graph M1 indicates a cross spectrum distorted by water absorption. The solid-line graph M2 indicates a cross spectrum corrected by the method according to the embodiment. As is obvious from FIG. 8B, according to the method of the embodiment, the distorted cross spectrum M1 is corrected into cross spectrum M2 that shows a substantially Gaussian shape.

The point spread functions corresponding to the two cross spectrums M1 and M2 are illustrated in FIG. 8C. Point spread functions N1 and N2 correspond to the cross spectrum M1 whose distortion is not corrected and to the cross spectrum M2 whose distortion is corrected, respectively. In the corrected point spread function N2, the side lobes n1 generated in the uncorrected point spread function N1 are suppressed. According to the correction indicated in the present example, the side robes are suppressed by an amount of about 18 dB.

Characteristics of the Embodiment(s)

Characteristics of the embodiment(s) are described. The following matters are not all the characteristics of the embodiment(s). Furthermore, it is sufficient for the embodiments to satisfy at least one of the following matters as characteristics.

Technology according to the embodiment(s) can be applied to any type of OCT. For example, the technology according to the embodiment(s) can be applied to OCT of a time domain system, a spectral domain system, or a swept source system.

The technology according to the embodiment(s) can be applied to any type of interference optical system. The technology according to the embodiment(s) can be applied to an interference optical system (a fiber optical system) using optical fibers as waveguides for the signal light and reference light, for example. In addition, the technology according to the embodiment(s) can also be applied to an interference optical system configured by arranging an optical element in a free space without using an optical fiber.

According to the technology of the embodiment(s) using the gain of optical amplifier(s), a 1-μm OCT with a light source including a spectrum ranging to the short wavelength of about 0.92 μm can be realized.

In the technology of the embodiment(s), an optical filtering function can be installed inside the reference arm to compensate for the distortion of spectral distribution caused by the object to the signal light. Thereby, without adding additional intensity loss to the signal light, it is possible to achieve both the suppression of side lobes and improvement of axial resolution. Such a function can be realized, for example, by simply providing a physical optical filter into the reference arm. Alternatively, it is also possible to combine the physical filtering with the data processing that involves a numerical filtering or window processing.

When the reference light has sufficient intensity at each wavelength, sufficient performance can be realized by numerical spectral shaping alone.

In ophthalmic OCT, its sensitivity is ultimately determined by the intensity of the reflected signal light. Accordingly, it is desirable to optimize the spectrum of the incident light so as to minimize the light loss due to water absorption without compromising an efficient bandwidth and the imaging capability influenced by the side lobes. In order to improve the transmission efficiency, the spectrum of the light beam incident into the eyes can also be changed.

EXAMPLE(S)

Example(s) using the abovementioned technology are described.
(Configuration)

Figure 9:
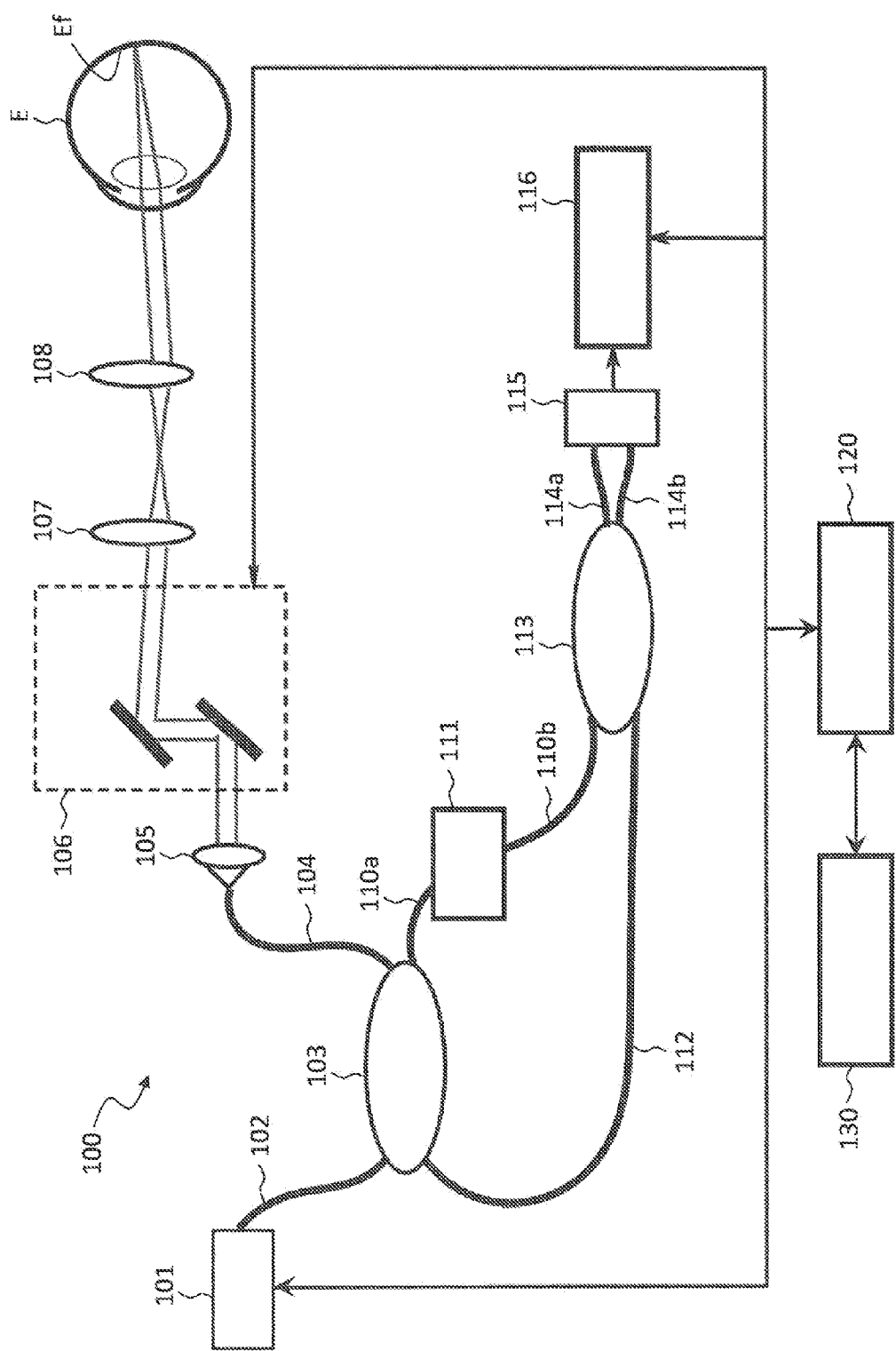
FIG. 9 is a schematic diagram showing an example of a structure of an embodiment of an optical imaging apparatus.

A configuration example of the optical imaging apparatus according to this embodiment(s) is illustrated in FIG. 9. Here, the apparatus using a swept source OCT method is described; however, a similar configuration can also be applied to the apparatus using time domain or spectral domain OCT method, as well. In the embodiment(s), the differences between an apparatus using swept source OCT method and the apparatus using other OCT method are merely the typical ones due to the differences among these different OCT methods. For example, in the time domain OCT and the spectral domain OCT, a broadband light source such as a SLD is used. In addition, in the spectral domain OCT, a sensor for detecting the spectral distribution of the interference light is used. As for this sensor, for example, a spectral radar can be used. A spectral radar includes a line scan camera, etc. In addition, with respect to the arithmetic processing on the detected data, a general arithmetic processing according to the OCT method to be applied is carried out. In addition, ophthalmic OCT is described here; however, OCT for other purposes can be configured without any substantial differences.

The optical imaging apparatus 100 illustrated in FIG. 9 has a light source unit 101 including a swept source such as a wavelength tunable laser. A swept source outputs the light while rapidly and continuously changing its output wavelength. In the event, for example, that a wavelength range is widely set, the light source unit 101 may include multiple swept sources having different wavelength bands. A method of carrying out OCT by synthesizing multiple light sources is well-known. In addition, in the case of utilizing multiple swept sources, it is possible to provide an optical interference system that takes each light source into consideration. For example, in the case of providing a swept source on the long wavelength side and a swept source on the short wavelength side, it is possible to set up separately an interference system on the long wavelength side and the other on the short wavelength side. In addition, the light source unit 101 may include a filter that changes the spectral distribution of output from the swept source. This filter is designed so as to deform the shape of the spectral distribution of output from the swept source into a Gaussian shape.

The light output from the light source unit 101 is transmitted to a fiber coupler 103 via an optical fiber 102. The fiber coupler 103 connects four optical fibers 102, 104, 110, and 112. Light transmitted via optical fiber 102 is divided into signal light and reference light by the fiber coupler 103. The signal light is the light that is transmitted via a predetermined path and incident onto the object. The signal light is also referred to as measurement light or sample light, etc. The reference light is combined with the signal light via a predetermined path.

The signal light is guided by the optical fiber 104 and output from its fiber end. This output is transformed into a parallel light beam by a collimator 105. The collimated signal light is then focused on the fundus Ef of the eye E via a scanner 106 by means of lenses 107 and 108. The scanner 106 varies the incidence position of the signal light onto the fundus Ef. As a scanner 106, a Galvano scanner, a polygon mirror, a resonant scanner, an acousto-optic modulator, a rotation prism, an oscillation prism, etc. can be used. An optical path formed by an optical fiber 104, a collimator 105, a scanner 106, and lenses 107 and 108 is referred to as a signal light path or a sample arm, etc.

The signal light projected onto the fundus Ef is scattered by various tissues of the fundus Ef. The back-scattered component of the scattered light is returned to the fiber coupler 103 via the signal light path. Further, this returned light is guided to a fiber coupler 113 by an optical fiber 112. This returned light contains the depth information of the fundus Ef.

On the other hand, the reference light created by the fiber coupler 103 is guided to a filter 111 by an optical fiber 110a. The filter 111 functions so as to deform the spectral distribution of the reference light, whose details will be described later. The reference light with a spectral distribution deformed by the filter 111 is guided to the fiber coupler 113 via an optical fiber 110b. Such a path of reference light is referred to as a reference light path or a reference arm, etc.

The fiber coupler 113 connects four optical fibers 110b, 112, 114a, and 114b. The coupling ratio of the fiber coupler 113 is 1:1, for example. The signal light and the reference light are superimposed with each other by the fiber coupler 113 to generate an interference light. This interference light contains the depth information of the fundus Ef carried by the signal light, and the spectral distribution information of the reference light deformed by the filter 111. The detector 115 detects the interference light guided by the optical fibers 114a and 114b. The detector 115, for example, is a balanced detector consisting of two balanced photo detectors to provide a differential output.

Whenever the interference light is detected, the detector 115 transmits the detection result (detected signals) to a data acquisition part 116. The data acquisition part 116 acquires the detected signals which are sequentially received from the detector 115. The data acquisition part 116 transmits these detected signals to an arithmetic and control unit 120 at the frequency of for example, each series of wavelength sweep, namely, the A-line scans.

The arithmetic and control unit 120 reconstructs each A-line profile (A-line image) using the abovementioned principle and the data to be input from the data acquisition part 116. Furthermore, the arithmetic and control unit 120 forms a B-scan image (tomographic image) by aligning multiple A-line profiles in a line corresponding to the scanning pattern of the signal light. In addition, the arithmetic and control unit 120 generates stack data by aligning the multiple B-scan images corresponding to the scanning pattern of the signal light, and by further performing an image processing such as interpolation processing to this stack data a volume data can be created.

A user interface (man-machine interface) 130 includes a display device, an input device, an operation device, etc. As a display device, LCD, etc. is used. As an input device and an operation device, various hardware devices (a switch, a button, a knob, a joy stick, etc.) arranged on the optical imaging apparatus 100 are considered. In addition, a hardware key (for example, a key board, a pointing device provided to a computer, etc.) arranged on an apparatus connected to the optical imaging apparatus 100 can be used as an input device and an operation device. Furthermore, a software key displayed on the abovementioned display device and the abovementioned computer can also be used as an input device and an operation device.

(With Respect to a Filter 111)

The filter 111 will be described. As described above, the filter 111 functions so as to deform the spectral distribution of the reference light. The filter 111 is configured (and/or controlled) so as to realize the abovementioned transmission function $T_r(\lambda)$ of the filter 1003. A configuration example of the filter 111 is described below.

Figure 10A:
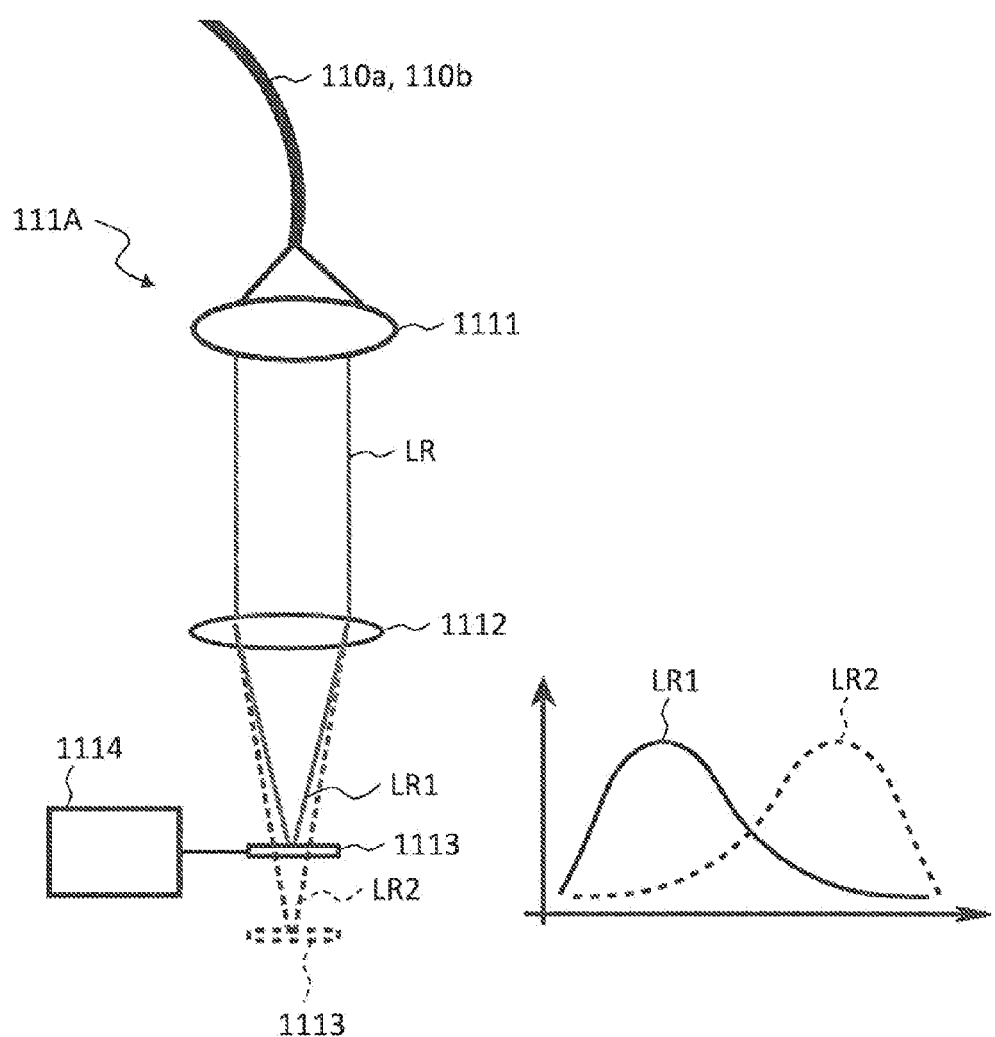
FIG. 10A is a schematic diagram showing an example of a structure of an embodiment of an optical imaging apparatus.

The first example of the filter 111 is illustrated in FIG. 10A. The filter 111A illustrated in FIG. 10A comprises a collimator 1111, a focusing lens 1112, a reference mirror 1113, and a drive mechanism 1114.

The collimator 1111 is arranged in the vicinity of the output end of the optical fiber 110a (the input end of the optical fiber 110b). The collimator 1111 converts the reference light LR output from the optical fiber 110a into a collimated light beam. In addition, the collimator 1111 couples part of the reference light LR that is reflected by a reference mirror 1113 into the optical fiber 110b.

The focusing lens 1112 converts the reference light LR that has been collimated by the collimator 1111 into a focusing light beam.

The reference mirror 1113 reflects the reference light LR that has been converted by the focusing lens 1112 into a focusing light beam. The drive mechanism 1114 shifts the reference mirror 1113 along the optical axis direction of the filter 111A (the propagation direction of the reference light LR). Thereby, the distance between the focusing lens 1112 and the reference mirror 1113 is varied. The drive mechanism 1114 comprises an actuator such as a pulse motor and components that transmit such a drive force generated by the actuator. In addition, the drive mechanism 1114 is controlled by the arithmetic and control unit 120 to be operated.

A means for moving the focusing lens 1112 and the reference mirror 1113 as a combined unit along the optical axis direction of the filter 111A may be provided. Thereby, the path length difference between the signal arm and the reference arm is varied, and the depth position of the object to be imaged is varied accordingly.

According to the filter 111A, by adjusting the position of the reference mirror 1113, it is possible to change the spectral distribution of the reference light LR reflected by the reference mirror 1113. This is a configuration utilizing a chromatic aberration of the focusing lens 1112. In other words, due to the effect of chromatic aberration, the reference light LR converted into a focusing beam by the focusing lens 1112 forms an image of its longer wavelength component at a deeper position from the focusing lens 1112. Therefore, if the reference mirror 1113 is placed at a position closer to the focusing lens 1112, the reflected light LR1 (solid line) will contain more of the short wavelength components of the reference light LR. In contrast, if the reference mirror 1113 is placed at a position further away from the focusing lens 1112, the reflected light LR2 (broken line) will contain more of the long wavelength components of the reference light LR. Spectral distributions of the reflected lights LR1 and LR2 are illustrated in the graph of FIG. 10A. In the event of carrying out OCT measurement, by placing the reference mirror 1113 at a position where the abovementioned transmission function $T_r(\lambda)$ of the filter 1003 is substantially realized, it is possible to optimize the spectral distribution of the reference light contributing to the generation of interference.

The second example of the filter 111 is illustrated in FIG. 10B. The filter 111B illustrated in FIG. 10B comprises a collimator 1115, an optical filter 1116, a focusing lens 1117, and a reference mirror 1118. The collimator 1115 is similar to the collimator 1111 of the first example. The focusing lens 1117 is similar to the focusing lens 1112 of the first example. The reference mirror 1118 is similar to the reference mirror 1113 of the first example; however, the reference mirror 1118 needs not to be movable.

The optical filter 1116 is customized so as to substantially realize the abovementioned transmission function $T_r(\lambda)$ of the filter 1003. The graph of FIG. 10B illustrates the spectral distribution of reference light LR3 before passing through the optical filter 1116 and the spectral distribution of reference light LR4 after passing through the optical filter 1116. By using this optical filter 1116, it is possible to optimize the spectral distribution of the reference light contributing to the generation of interference.

The configuration of the filter 111 is not limited to those described above and any specific configuration is available if it functions to optimize the spectral distribution of the reference light contributing to the generation of interference. For example, a diffraction grating having a reflecting surface whose shape is capable of optimizing the spectral distribution of the reference light can be used. As a configuration example for this, a diffraction grating with a reflecting surface formed so as to have the abovementioned shape can be used. In addition, it is also possible to realize a configuration that can reform the shape of the reflecting surface of a diffraction grating. This configuration, for example, uses the MEMS (Micro Electro Mechanical Systems) technology.

(Optical Imaging Apparatus and Optical Imaging Method)

Characteristics of the above-described apparatus and the method thereof are summarized as follows.

The first configuration example of the optical imaging apparatus is described. This optical imaging apparatus is an apparatus that divides the light output from a light source unit into a signal light and a reference light, detects the interference light generated by superimposing the signal light having passed through an object onto the reference light, and forms a tomographic image of the object based on the detection result. The light source unit (101) outputs light with a wavelength range corresponding to the coordinates positioned within a region whose border is a contour line indicating a predetermined light loss amount based on the distribution information of the light loss amount due to absorption by a medium that is predefined in a space spanned by a first coordinate axis (the horizontal axis in FIG. 3) indicating a representative wavelength and a second coordinate axis (the vertical axis in FIG. 3) indicating a wavelength range including the representative wavelength.

The method applied to this optical imaging apparatus (an optical imaging method) includes the following steps:

(i) outputting light within a wavelength range corresponding to the coordinates positioned within a region whose border is a contour line indicating a predetermined light loss amount based on the distribution information of the light loss amount due to absorption by a medium that is predefined in a space spanned by a first coordinate axis indicating a representative wavelength and a second coordinate axis indicating a wavelength range including the representative wavelength;

(ii) dividing the output light into signal light and reference light;

(iii) generating the interference light by superimposing the signal light having passed through an object onto the reference light;

(iv) detecting the generated interference light; and (v) forming a tomographic image of the object based on the detection result of the interference light.

The contour line as a border line in these optical imaging apparatuses and optical imaging method is arbitrarily set. For example, when the medium is substantially water, the coordinates may be the coordinates on a contour line B4 (refer to FIG. 3) indicating a region in which the excess loss amount over a reference loss amount illustrated in FIG. 2 is 4 dB and the contour line B4 is passing through the coordinates in the vicinity of a value of 1124 nm on the first coordinate axis, or the coordinates positioned in the negative direction (shorter wavelength) of the first coordinate axis as compared to the contour line B4.

In addition, the component of the coordinates corresponding to the first coordinate axis may be substantially 1050 nm. In other words, arbitrary coordinates on a line illustrated by the broken line in FIG. 3, (representative wavelength, wavelength range)=(1050, Δλ), can be applied. In the event of applying 1050 nm as a representative wavelength, a wavelength range (axial resolution) can be arbitrarily set without much limitation due to the excess loss. In other words, even if the wavelength range is arbitrarily widened, it is possible to limit the excess loss amount within a range of no more than 3 dB. Therefore, by setting a representative wavelength at 1050 nm, it is possible to increase the freedom in the setting of wavelength range.

The second configuration example of the optical imaging apparatus is described. This optical imaging apparatus is an apparatus that divides the output from a light source unit (101) into a signal light and a reference light, detects the interference light generated by superimposing the signal light having passed through an object onto the reference light, and forms a tomographic image of the object based on the detection result. Furthermore, this optical imaging apparatus comprises a storage part configured to store in advance the relation information in which a representative wavelength, a wavelength range including the representative wavelength, and the light loss amount due to absorption by a medium are related to each other. This storage part comprises, for example, a storage device (hard disk drive, ROM, etc.) included in the arithmetic and control unit 120. The relation information may be continuous information such as the distribution information illustrated in FIG. 3, or it may be discrete information such as the information listed in a table. The light source unit (101) outputs light including a wavelength range predetermined based on the relation information.

The method (optical imaging method) applied to this optical imaging apparatus includes the following steps:

(i) determining a representative wavelength and a wavelength range including the representative wavelength based on the relation information in which the representative wavelength, the wavelength range including the representative wavelength, and the light loss amount due to absorption by a medium are related to each other;

(ii) outputting light including the determined wavelength range;

(iii) dividing the output light into a signal light and a reference light;

(iv) generating interference light by superimposing the signal light having passed through an object onto the reference light;

(v) detecting the generated interference light; and (vi) forming a tomographic image of the object based on the detection result of the interference light.

The step for determining a representative wavelength and a wavelength range is carried out, for example, by referring to the distribution information (an example of the relation information) as illustrated in FIG. 3 and taking into consideration the representative wavelength, the wavelength range, and the light loss amount entirely, or taking into consideration the representative wavelength, the wavelength range, and the light loss amount according to the desired order of priority. The arithmetic and control unit 120 enables a display device of the user interface 130 to display an interface for carrying out the abovementioned determination operation thereon. The user inputs the values of parameters through an operation device and an input device, etc. As an example of an interface to be displayed, the distribution information as illustrated in FIG. 3 is chosen. The user can designate the desired coordinates in the distribution information using a pointing device. In addition, it is possible to configure to display an input space on the display device for inputting parameters, and allow the user to input the desired values using a keyboard, etc. In addition, it is also possible to configure to display an interface (a pull-down menu, etc.) capable of providing the parameter selection options, and allow the user to designate the desired values using a pointing device, etc. it should be noted that since the relation information relates the abovementioned three parameters to each other, if the user determines the values for any two among these three parameters, the value of the third parameter can be determined by the arithmetic and control unit 120. The arithmetic and control unit 120 can cause the display device to display the determined value thereon. Thereby, the user can carry out the determination operation of the representative wavelength and the wavelength range while taking into consideration the values of the three parameters.

The third configuration example of the optical imaging apparatus is described. This optical imaging apparatus is an apparatus that divides the light output from a light source unit (101) into a signal light and a reference light, detects the interference light generated by superimposing the signal light having passed through an object onto the reference light, and forms a tomographic image of the object based on the detection result. Furthermore, this optical imaging apparatus comprises an optical component that converts the spectral distribution of the reference light such that the interference light based on the signal light having passed through a medium (object) will achieve a predetermined spectral distribution. This optical component corresponds to the filter 111 illustrated in FIG. 9.

The method (an optical imaging method) applied to this optical imaging apparatus includes the following steps:
(i) outputting light,
(ii) dividing the output light into a signal light and a reference light;
(iii) reshaping the spectral distribution of the reference light such that the interference light based on the signal light having passed through a medium (object) achieves a predetermined spectral distribution;
(iv) generating the interference light by superimposing the signal light having passed through the object onto the reference light whose spectral distribution has been reshaped;
(v) detecting the generated interference light; and
(vi) forming a tomographic image of the object based on the detection result of the interference light.

(Apparatus for Setting the Characteristics of a Light Source and a Method for Setting the Characteristics of a Light Source)

In order to set the characteristics of a light source unit used in the optical imaging apparatus and the optical imaging method, technology according to the embodiment(s) can be applied. Specifically, the following apparatus and method are realized. It should be noted that the characteristics of the light source unit indicate a representative wavelength and a wavelength range.

The apparatus for setting the specifications of a light source comprises a storage part, a setting part, an acquiring part, and an output part. The storage part stores in advance the relation information in which a representative wavelength and a wavelength range including the representative wavelength of light to be output from a light source unit for the use in optical coherence tomography, and the light loss amount due to absorption by a medium are related to each other. The setting part sets each value of a first parameter and a second parameter among the representative wavelength, wavelength range, and light loss amount. The first parameter and the second parameter represent any two parameters among these three parameters. The acquiring part acquires the value of the third parameter based on the two values set by the setting part and the relation information. The third parameter represents the parameter among the representative wavelength, the wavelength range, and the light loss amount other than the first parameter and the second parameter. The output part outputs the value of the third parameter acquired by the acquiring part. An output aspect of the output part is arbitrary. An example of the output aspect includes display output, print output, transmission output, storage output, etc. The display output is an information display process by means of a display device. The print output is a process for fixing the information onto a sheet of paper. The transmission output is an information transmission process using wire communication or wireless communication. The storage output is a process for storing the information in a storage device installed inside or outside the apparatus.

The method applied to this apparatus for setting the specifications of a light source (method for setting characteristics of a light source) is a method that employs a computer to set the characteristics of the light beam to be output from a light source unit for the use in optical coherence tomography. The method comprises the following steps:
(i) causing a computer to store the relation information in which a representative wavelength, a wavelength range including the representative wavelength, and the light loss amount due to absorption by a medium are related to each other;
(ii) setting each value of a first parameter and a second parameter among the representative wavelength, the wavelength range, and the light loss amount;
(iii) acquiring the value of the third parameter among the representative wavelength, the wavelength range, and the light loss amount other than the first parameter and the second parameter, based on the two set values and the relation information; and
(iv) outputting the value of the acquired third parameter.

Figure 11:
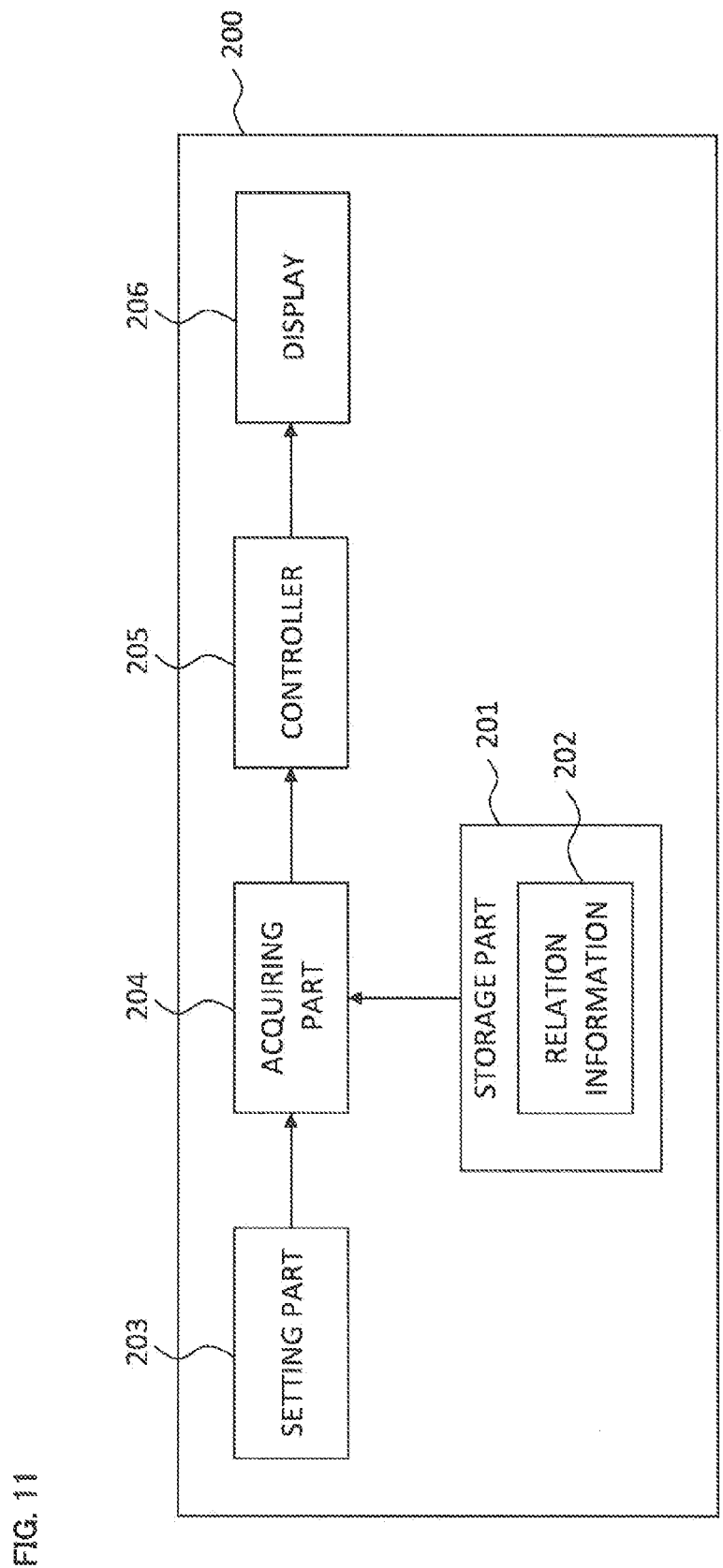
FIG. 11 is a schematic diagram showing an example of a structure of an embodiment of an apparatus for setting the characteristics of a light source.

An example of the apparatus for setting the specifications of a light source is illustrated in FIG. 11. The apparatus for setting the characteristics of a light source 200 comprises a storage part 201, a setting part 203, an acquiring part 204, a controller 205, and a display 206. In the apparatus for setting the characteristics of a light source 200, the display output is applied as the output aspect of the output part. Furthermore, in the case of applying other output aspects, a configuration in accordance with it is provided. For example, in the case of printing output, a print part (a printer) is provided, in the case of transferring output, a communication part (a communication interface) is provided, and in the case of storing output, a storage part or communication part is provided. In addition, the controller 205 controls the output part in accordance with the applied output aspect.

In the storage part 201, the relation information 202 is stored in advance. The relation information 202 is, for example, the distribution information as indicated in FIG. 3, or the discrete information such as that listed in a table.

The setting part 203 includes, for example, a display device and an operation device. On the display device, a predetermined interface (GUI, etc.) is displayed by the controller 205. The interface and parameter setting method are, for example, similar to those described above. Using the setting part 203, the user sets each value of a first parameter and a second parameter among the representative wavelength, the wavelength range, and the light loss amount.

The acquiring part 204 reads the relation information 202 from the storage part 201. Furthermore, the content set by the setting part 203, namely the set values of the first parameter and the second parameter, are input into the acquiring part 204. With reference to the relation information 202, the acquiring part 204 acquires the value of the third parameter related to the two set values. For example, in the event that a representative wavelength of 1050 nm and a wavelength range of 117 nm are set, the acquiring part 204 acquires an (excess) light loss amount of 2 dB corresponding to these set values. In addition, when a representative wavelength of 1050 nm and an (excess) light loss amount of 2 dB are set, the acquiring part 204 acquires a wavelength range of 117 nm corresponding to these set values. In addition, when a wavelength range of 117 nm and an (excess) light loss amount of 2 dB are set, the acquiring part 204 acquires a representative wavelength of 1050 nm corresponding to these set values.

In the controller 205, the value of the third parameter acquired by the acquiring part 204 (and each value of the first parameter and the second parameter) is input. The controller 205 causes the display 206 to display this third parameter value (and each value of the first parameter and the second parameter) thereon. Here, in the case of display output, in general, each value of the first parameter and the second parameter has already been displayed, such that, at this output control stage, display control is carried out only on the value of the third parameter. In contrast, in the event of other output aspects, it is possible to output the values of the three parameters.

There is a case in which the apparatus for setting the specifications of a light source 200 is a server and the user may carry out a parameter setting operation using a client computer capable of communicating with this server. In this case, the setting part 203 does not necessarily include a display device and an operation device, but includes a communication interface that receives setting information from the client computer. Further, the output part in this case includes a communication interface to carry out data transmission. In general, since each value of the first parameter and the second parameter has already been displayed by the client computer, the controller 205 may be configured to control the output part so as to transmit only the value of the third parameter acquired by the acquiring part 204 to the client computer.

According to the apparatus for setting the specifications of a light source and the method for setting the characteristics of a light source in this embodiment, it is possible to preferably and easily set the characteristics of the light source unit for optical coherence tomography. It should be noted that the apparatus and the method can be used for designing the optical imaging apparatus.

In addition, such a function for setting the characteristics of a light source can also be provided with the optical imaging apparatus. In this case, in accordance with the characteristics of an object and a measurement mode, etc., the light characteristics of light to be output from the light source unit can be set. Furthermore, the optical imaging apparatus is configured so as to be capable of switching the deformation mode for a reshaping of the spectral distribution of the reference light in accordance with a set content of characteristics. This switching of deformation mode for a reshaping of the spectral distribution can be made, for example, by switching the position of the reference mirror 1113 illustrated in FIG. 10A, switching the arrangement of the optical filter 1116 illustrated in FIG. 10B, and switching the shape of the reflecting surface of the diffraction grating using MEMS, etc. Furthermore, the switching arrangement of the optical filter 1116 can be realized, for example, by using a turret plate that is provided with multiple optical filters with different transmission characteristics, and a filter drive mechanism for rotating this turret plane.

It is possible to configure the apparatus so as to carry out such a switching action automatically. For example, association information for associating parameters of a light source characteristics (a representative wavelength and a wavelength range) with the deformation contents of a spectral distribution (the position of the reference mirror 1113, the optical filter 1116 selectively placed inside the reference arm, and the shape of the reflecting surface of the diffraction grating, etc.) are stored in the storage part 201 in advance. When the representative wavelength and the wavelength range are set, the controller 205, with reference to the association information, specifies the deformation contents corresponding to the set contents. Then, based on the specified deformation contents, the controller 205 controls the reference mirror 1113 (the drive mechanism 1114), the optical filter 1116 (the filter drive mechanism), and the shape of the reflecting surface of the diffraction grating (MEMS), etc.

The embodiments described above are merely examples for favorably implementing the present invention. Therefore, it is possible to properly make arbitrary modifications (omission, substitution, addition, etc.) within the scope of the present invention.

Computer programs for realizing the above embodiments can be stored in any kind of recording medium that can be read by a computer. As this recording medium, for example, an optical disk, a magneto-optic disk (CD-ROM, DVD-RAM, DVD-ROM, MO, and so on), and a magnetic storage (a hard disk, a Floppy Disk™, ZIP, and so on) can be used.

Besides, it is possible to transmit/receive this program through a network such as internet or LAN, etc.

What is claimed is:

1. An optical imaging method, comprising the steps of:
   determining a representative wavelength and a wavelength range including said representative wavelength based on relation information in which a representative wavelength, a wavelength range including this representative wavelength, and the light loss amount due to absorption by a medium are related to each other;
   outputting light including the determined wavelength range;
   dividing the output light into signal light and reference light;
   generating interference light by superimposing the signal light having passed through an object onto the reference light;
   detecting the generated interference light; and
   forming a tomographic image of the object based on the detection result of the interference light,
   wherein the relation information is information indicating that the light loss amount changes depending on the wavelength range even if a value of the representative wavelength is the same or information indicating that the light loss amount changes depending on the wavelength even if the wavelength range is the same, and
   the representative wavelength, the wavelength range, and the light loss amount of the output light are based on a result from arbitrarily setting two of the representative wavelength, the wavelength range, and the light loss amount to determine a third of the representative wavelength, the wavelength range, and the light loss amount.

2. The optical imaging method according to claim 1, further comprising:
   converting the spectral distribution of the reference light into a predetermined spectral distribution such that a distortion of a spectrum distribution due to absorption by said medium is compensated in the spectral distribution of the interference light based on the signal light having passed through said medium, by using the relation information, and
   wherein the interference light is generated by superimposing the signal light having passed through an object onto the reference light whose spectral distribution has been converted.

* * * * *